(12) United States Patent
Traynor-Kaplan et al.

(10) Patent No.: US 6,221,856 B1
(45) Date of Patent: Apr. 24, 2001

(54) INOSITOL DERIVATIVES FOR INHIBITING SUPEROXIDE ANION PRODUCTION

(75) Inventors: Alexis E. Traynor-Kaplan, North Bend, WA (US); Carsten Schultz, Bremen; Marco T. Rudolf, Hamburg, both of (DE)

(73) Assignees: Inologic, Inc., North Bend, WA (US); Regents of the University of California, Oakland, CA (US)

( * ) Notice: Subject to any disclaimer, the term of this patent is extended or adjusted under 35 U.S.C. 154(b) by 0 days.

(21) Appl. No.: 09/244,087

(22) Filed: Feb. 3, 1999

(51) Int. Cl.$^7$ .................................................. A01N 57/00

(52) U.S. Cl. ........................ 514/103; 514/102; 514/110; 554/78; 554/229

(58) Field of Search ...................... 554/78, 229; 514/102, 514/103, 110

(56) References Cited

U.S. PATENT DOCUMENTS

| | | |
|---|---|---|
| 4,952,396 | 8/1990 | Sabin et al. . |
| 5,019,566 | 5/1991 | Siren . |
| 5,051,411 | 9/1991 | Siren . |
| 5,128,332 | 7/1992 | Siren et al. . |
| 5,342,832 | 8/1994 | Siren . |
| 5,434,144 | 7/1995 | Kasting et al. . |
| 5,552,148 | 9/1996 | Znaiden et al. . |
| 5,614,511 | 3/1997 | Znaiden et al. . |
| 5,693,521 | 12/1997 | Tsien et al. . |

FOREIGN PATENT DOCUMENTS

| | | |
|---|---|---|
| WO 96/40695 | 12/1996 | (WO) . |
| WO 98/11901 | 3/1998 | (WO) . |
| WO 98/26786 | 6/1998 | (WO) . |

OTHER PUBLICATIONS

Badwey et al., 1982, "Cytochalasin E Diminishes the Lag Phase in the Release of Superoxide by Human Neutrophils", Biochem. Biophys. Res. Comm. 106:170–174.

Bae et al., 1997, "Epidermal Growth Factor (EGF)–Induced Generation of Hydrogen Peroxide", J. Biol. Chem. 272:217–221.

Brewster et al., 1993, "Chemical Approaches to Brain–Targeting of Biologically Active Compounds", in: *Drug Design for Neuroscience*, Kozikowski, ed., Raven Press, NY, NY, pp. 435–467.

Cerutti and Trump, 1991, "Inflammation and Oxidative Stress in Carcinogenesis", Cancer Cells 3:1–7.

Clayson, 1994, "Mechanistic and Other Considerations in Cancer Prevention", Cancer Lett. 83:15–19.

Darveau, 1999, "Infection, Inflammation, and Cancer", Nature Biotechnol. 17:19.

Dipali et al., 1996, "Comparitive Study of Separation of Non–Encapsulated Drug from Unilamellar Liposomes by Various Methods", J. Pharm. Pharmacol. 48:1112–1115.

Dobos et al., 1992, "C5a Reduces Formyl Peptide–Induced Actin Polymerization and Phosphatidylinositol(3,4,5)triphosphate Formation, but not Phosphatidylinositol(4,5)biphosphate Hydrolysis and Superoxide Production, in Human Neutrophilis", J. Immunol. 149:609–614.

(List continued on next page.)

*Primary Examiner*—Deborah Carr
(74) *Attorney, Agent, or Firm*—Christensen O'Connor Johnson Kindness PLLC

(57) ABSTRACT

Inositol derivatives, compositions comprising inositol derivatives, and methods for using compositions comprising inositol derivatives as agents for inhibiting superoxide anion production are described. The inositol derivatives are obtainable via conventional organic synthesis. The inositol derivatives inhibit superoxide anion produced by neutrophils and macrophages which cause tissue damage.

50 Claims, 4 Drawing Sheets

OTHER PUBLICATIONS

Figure 1:
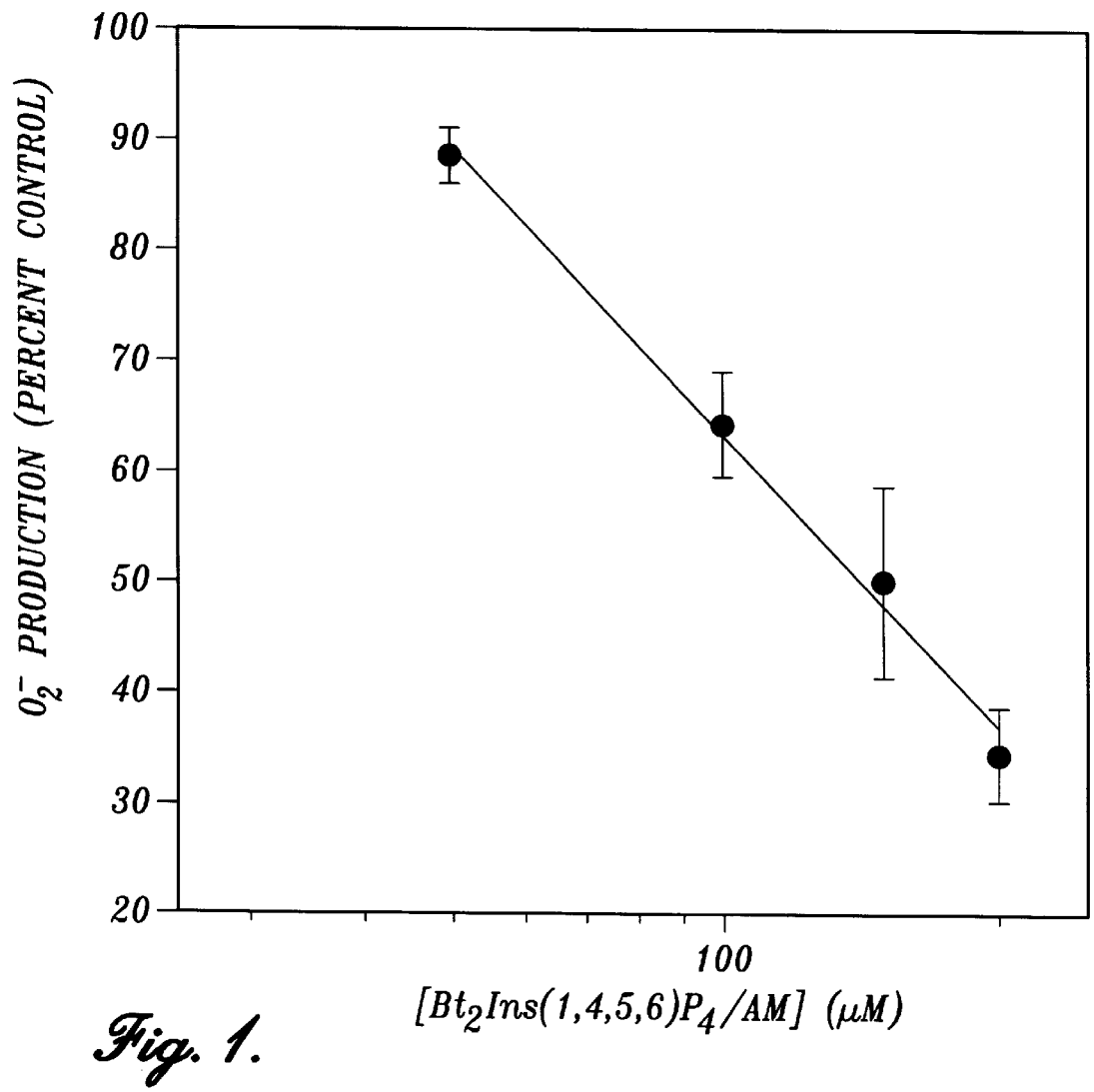

Eckmann et al., 1997, "D–myo–Inositol 1,4,5,6–Tetrakisphosphate Produced in Human Intestinal Epithelial Cells in Response to Salmonella Invasion Inhibits Phosphoinositide 3–Kinase Signaling Pathways", Proc. Natl. Acad. Sci. USA 94:14456–14460.

Evans, 1993, "Free Radicals in Brain Metabolism and Pathology", Brit. Med. Bull. 49:577–587.

Gregoriadis, 1989, "The Physiology of the Liposome", NIPS 4:146–151.

Hernandez et al., 1987, "Determination of the Encapsulation Efficiency in Liposomes Obtained by the 'Extruder Method'", J. Microencapsulation 4:315–320.

Hope et al., 1985, "Production of Large Unilamellar Vesicles by a Rapid Extrusion Procedure. Characterization of Size Distribution, Trapped Volume and Ability to Maintain a Membrane Potential", Biochim. Biophys. Acta 812:55–65.

Jackson and Cochrane, 1988, "Leukocyte–Induced Tissue Injury", Hematology/Oncology Clinics of North America 2:317–334.

Jenner and Olanow, 1996, "Oxidative Stress and the Pathogenesis of Parkinson's Disease", Neurology 47(Suppl. 3):S161–S170.

Jiang et al., 1998, "Membrane–Permanent Esters of Phosphatidylinositol 3,4,5–Triphosphate", J. Biol. Chem. 273: 11017–11024.

Joseph, 1992, "The Putative Role of Free Radicals in the Loss of Neuronal Functioning in Senescence", Integrative Physiological and Behavioral Sci. 27:216–227.

Keller and Mattson, 1998, "Roles of Lipid Peroxidation in Modulation of Cellular Signaling Pathways, Cell Dysfunction, and Death in the Nervous System", Reviews in the Neurosciences 9:105–116.

Korchak et al., 1998, "Selective Role for β–Protein Kinase C in Signaling for $O_2$ Generation but not Degranulation or Adherence in Differentiated HL60 Cells", J. Biol. Chem. 273:27292–27299.

Leib et al., 1996, "Reactive Oxygen Intermediates Contribute to Necrotic and Apoptotic Neuronal Injury in an Infant Rat Model of Bacterial Meningitis Due to Group B Streptococci", J. Clin. Invest. 98:2632–2639.

Li et al., 1997, "Membrane–Permeant Esters of Inositol Polyphosphates, Chemical Syntheses and Biological Applications", Tetrahedron 53:12017–12040.

Low et al., 1999, "Lipid A Mutant Salmonella with Suppressed Virulence and TNFα Induction Retain Tumor–Targeting in vivo", Nature Biotechnol. 17:37–41.

Markesbery, 1997, "Oxidative Stress Hypothesis in Alzheimer's Disease", Free Radical Biol. And Med. 23:134–147.

Maunder and Hudson, 1992, "Management of the Adult Respiratory Distress Syndrome", in: *Textbook of Internal Medicine*, 2$^{nd}$ ed., Kelley, ed., Lippincott Co., Philadelphia, PA, pp. 1862–1863.

Mayo and Curnutte, 1990, "Kinetic Microplate Assay for Superoxide Production by Neutrophils and Other Phagocytic Cells", Meth. Enzymol. 186:567–575.

McGeer and McGeer, 1998, "Mechanisms of Cell Death in Alzheimer Disease– Immunopathology", J. Neural Transm. Suppl. 54:159–166.

Miller and Britigan, 1995, "The Formation and Biologic Significance of Phagocyte–Derived Oxidants", J. Investigative Med. 43:39–49.

Roemer et al., 1996, "Membrane–Permeant Analogues of the Putative Second Messenger myo–Inositol 3,4,5,6–Tetrakisphosphate", J. Chem. Soc. Perkin Trans. 1:1683–1694.

Rudolf et al., 1998, "A Membrane–Permeant, Bioactivatable Derivative of INS(1,3,4)$P_3$ and Its Effect on Cl$^-$ Secretion from $T_{84}$ Cells", Bioorg. Med. Chem. 8:1857–1860.

Rudolf et al., 1998, "A 2–Deoxy Derivative is a Partial Agonist of the Intracellular Messenger Inositol 3,4,5,6–Tetrakisphosphate in the Epithelia Cell Line $T_{84}$", J. Med. Chem. 41:3635–3644.

Schultz et al., 1998, "Membrane–Permeant, Bioactivatable Derivatives of Inositol Polyphosphates and Phosphoinositides", Chapter XX in: *Phosphoinositides: Chemistry,Biochemistry and Biomedical Applications*, Bruzik, ed., Am. Chem. Soc. Symp. Ser. 718:232–243.

Sundaresan et al., 1995, "Requirement for Generation of $H_2O_2$ for Platelet–Derived Growth Factor Signal Transduction", Science 270:296–299.

Traynor–Kaplan et al., 1998, "An Inositol Tetrakisphosphate–Containing Phospholipid in Activated Neutrophils", Nature 334:353–356.

Traynor–Kaplan et al., 1989, "Transient Increase in Phosphatidylinositol 3,4–Bisphosphate and Phosphatidylinositol Trisphosphate During Activation of Human Neutrophils", J. Biol. Chem. 264:15668–15673.

Traynor–Kaplan et al., 1997, "Hydrogen Peroxide Inhibits Secretion by Colonic and Pancreatic Secretory Epithelia", Gastroenterology A412.

Uribe et al., 1996, "Phosphatidylinositol 3–Kinase Mediates the Inhibitory Effect of Epidermal Growth Factor on Calcium–Dependent Chloride Secretion", J. Biol. Chem. 271:26588–26595.

Vajanaphanich et al., 1994, "Long–Term Uncoupling of Chloride Secretion from Intracellular Calcium Levels by Ins(3,4,5,6)$P_4$", Nature 371:711–714.

Zhang et al., 1998, "Hydrogen Peroxide Stimulates Extracellular Signal–Regulated Protein Kinases in Pulmonary Arterial Smooth Muscle Cells", Am. J. Respir. Cell Mol. Biol. 19:324–332.

Cecil. 1988, *Textbook of Medicine*, 18$^{th}$ Edition, Wyngaarden and Smith, eds., W.B. Saunders Co., p. 1992.

INOSITOL DERIVATIVES FOR INHIBITING SUPEROXIDE ANION PRODUCTION

TABLE OF CONTENTS

|     | Page |
| --- | --- |
| 1. FIELD OF THE INVENTION | 1 |
| 2. BACKGROUND OF THE INVENTION | 1 |
| 3. SUMMARY OF THE INVENTION | 4 |
| 4. DESCRIPTION OF THE FIGS. | 13 |
| 5. DETAILED DESCRIPTION OF THE INVENTION | 13 |
|     5.1. INOSITOL DERIVATIVES | 13 |
|     5.2. SYNTHESIS OF THE INOSITOL DERIVATIVES | 16 |
|         5.2.1. THE COMPOUNDS OF FORMULA (I) | 16 |
|         5.2.2. THE COMPOUNDS OF FORMULA (II) | 19 |
| 6. METHODS FOR USE OF THE INOSITOL DERIVATIVES | 20 |
| 7. EXAMPLE: INHIBITION OF f-METHIONINE-LEUCINE-PHENYLALANINE-STIMULATED SUPEROXIDE ANION PRODUCTION IN HUMAN NEUTROPHILS BY D-2,3-DI-O-BUTYRYL-MYO-INOSITOL 1,4,5,6-TETRAKISPHOSPHATE OCTAKIS(ACETOXYMETHYL)ESTER | 28 |
| 8. EXAMPLE: INHIBITION OF f-METHIONINE-LEUCINE-PHENYLALANINE-STIMULATED SUPEROXIDE ANION PRODUCTION IN HUMAN NEUTROPHILS BY SN-DI-O-PALMITOYL-D,L-6-O-BUTYRYL-PHOSPHATIDYLINO-SITOL 3,4,5,-TRISPHOSPHATE HEPTAKIS(ACETOXYMETHYL)ESTER | 29 |
| 9. EXAMPLE: INHIBITION OF f-METHIONINE-LEUCINE-PHENYLALANINE-STIMULATED SUPEROXIDE ANION PRODUCTION IN HUMAN NEUTROPHILS BY D-2,3-DI-O-BUTYRYL-MYO-INOSITOL 1,4,5,6-TETRAKISPHOSPHATE OCTAKIS(ACETOXYMETHYL)ESTER AND D-2,3-DI-O-BUTYRYL-MYO-INOSITOL 1,4,5,6-TETRAKISPHOSPHATE OCTAKIS(ACETOXYMETHYL)ESTER + SN-DI-O-PALMITOL-D,L,6,O-BUTYRYL-PHOSPHATIDYLINO-SITOL 3,4,5-TRISPHOSPHATE HEPTAKIS(ACETOXYMETHYL)ESTER | 30 |
| 10. EXAMPLE: INHIBITION OF f-METHIONINE-LEUCINE-PHENYLALANINE- OR PHORBOL ESTER-STIMULATED SUPEROXIDE ANION PRODUCTION IN HUMAN NEUTROPHILS BY SN-DI-O-PALMITOL-D,L-6-O-BUTYRYL-PHOSPHATIDYLINOSITOL 3,4,5-TRISPHOSPHATE HEPTAKIS(ACETOXYMETHYL)ESTER | 32 |
| 11. EXAMPLE: PRODUCTION OF PHOSPHATIDYLINO-SITOL 3,4,5-TRISPHOSPHATE BY f-METHIONINE-LEUCINE-PHENYLALANINE-STIMULATED NEUTROPHILS OF A CROHN'S DISEASE PATIENT | 33 |
| ABSTRACT | 50 |

1. FIELD OF THE INVENTION

The present invention was made with government support under grant no. 1RO1-DK47240–01A1 awarded by the National Institutes of Health. The government has certain rights in the invention.

The present invention relates to inositol derivatives that inhibit the production of superoxde anion, which can result from inflammation and from non-inflammatory conditions and which can lead to oxidative damage of tissues and pathological conditions. The present invention also relates to compositions comprising the inositol derivatives and methods for their use for preventing or treating in mammals conditions such as inflammation that cause superoxide anion production, oxidative damage of tissues, and pathological conditions caused by superoxide anion production.

2. BACKGROUND OF THE INVENTION

Superoxide anion is formed by macrophages and polymorphonuclear leukocytes, also known as neutrophils as a byproduct of oxygen metabolism. Macrophages and neutrophils are distributed throughout most tissues and play a role in inflammation, in host defense, and in reactions against a number of autologous and foreign substances. As major players in the inflammatory response, they are attracted to sites of injury or disease by cytokines released at these sites. While superoxide anion can function as a microbicidal agent that helps degrade tissue damaged from external or internal trauma, it can also have destructive effects. The presence of superoxide anion can lead to the formation of other reactive and tissue-damaging species such as HOCl and $H_2O_2$. In the presence of $Fe^{2+}$, $H_2O_2$ can proceed to form hydroxyl radical which can be highly destructive to surrounding tissue.

Superoxide anion is produced in response to inflammation or of non-inflammatory conditions, such as adult respiratory distress syndrome, and can lead to significant tissue injury (S. L. Leib et al., *J. Clin. Invest.* 98(1 1):2632–2639 (1996); R. A. Miller et al., *J. Invest. Med.* 43(1):39 (1995); and J. Jackson et al., *Hematology/Oncology Clinics of North America* 2(2):317–34 (1988)). Inflammation accompanies a variety of disorders, including eczema, inflammatory bowel disease, rheumatoid arthritis, asthma, psoriasis, ischemia/reperfusion injury, ulcerative colitis and acute respiratory distress syndrome. These disorders can be chronic and, in severe cases, life-threatening. In addition, acute inflammation can follow a heart attack or stroke and often results in irreparable damage to surrounding tissue.

Exposure of tissues to superoxide anion radical can lead to oxidative stress and tissue damage, which can contribute to the development of pathological conditions. Superoxide anion can act as a carcinogen causing oxidant-induced DNA sequence changes that affect the activities of proto-oncogenes and supressor genes and activating cellular kinases to promote cell growth (Cerutti and Trump, *Cancer Cells* 3:1–7 (1991)). The production of superoxide anion and other free radicals can lead to demyelination or neuronal death and conditions such as multiple sclerosis, the deterioration of cognitive function with aging, dementia, amyotropic lateral sclerosis ("ALS"), Alzheimer's disease, Parkinson's disease, and other degenerative neuropathies. (Keller and Mattson, *Rev. Neurosci.* 9:105–116 (1998); McGeer and McGeer, *J. Neural. Transm. Suppl.* 54: 159–166 (1998); Markesbery, *Free Radic. Biol. Med.* 23:13447 (1997); Jenner and Olanow, *Neurology* 47(6Suppl 3):S161–70 (1996); Evans, *Br. Med. Bull.* 49:577–87 (1993); Joseph, *Integr. Physiol. Behav. Sci.* 27:216–27 (1992)).

Current therapies for conditions that result from oxidative tissue damage are either non-existent or fraught with drawbacks. First, while these therapies may act to reduce the degree of tissue swelling that accompanies inflammation, these therapies do not inhibit the formation of tissue-damaging superoxide anion, $H_2O_2$ or HOCl. Second, therapies involving the administration of anti-inflammatory steroids can cause undesirable immunosuppression and, in fact, premature atrophy of the thymus gland. Third, therapies involving a prolonged use of salicylates or other non-steroidal anti-inflammatory drugs can result in gastrointestinal bleeding. Fourth, therapies used for the treatment of asthma that involve repeated and frequent use of bronchiodialators can result in drug tolerance and a need for increased dosages and/or alternative drugs. Therapies for cancer are far fewer in number, have serious drawbacks, and have limited efficacy. Chemotherapy can be highly toxic, resulting in fatigue, vomiting, hair loss, and immunosuppression. Radiation therapy can lead to burns and localized immunosuppression. Excision of cancerous lesions can be highly invasive. Therapies for degenerative neuropathies are virtually non-existent. Although it is possible to use chemicals to slow nerve degeneration, methods for completely halting or reversing the damage have not yet been elucidated.

Thus, there is a clear need for agents that inhibit superoxide anion production, thereby treating or preventing conditions resulting from oxidative tissue damage without causing the above-mentioned, undesirable side-effects.

Phosphatidylinositol 3,4,5-trisphosphate has been isolated from FLPEP-stimulated human neutrophils (A. E. Traynor-Kaplan et al., *J. Biol. Chem.* 264(26):15668–15673 (1989) and A. E. Traynor-Kaplan et al., *Nature* 334(6180) :353–56 (1988)). It has recently been shown that certain inositol phosphate derivatives including D-myoinositol 3,4, 5,6-tetrakisphosphate (A. Vajanaphanich et al., *Nature* 371:711 (1994); J. M. Uribe et al., *J. Biol. Chem.* 271(43) :26588 (1996); M. T. Rudolf et al., *J. Med. Chem.* 41 (19):3635–3644 (1998)), and sn-di-O-pahmitoyl-D,L-6-O-butyryl-phosphatidylinositol 3,4,5-trisphosphate heptakis (acetoxymethyl)ester (C. Schultz et al., *Membrane-penneant*, Bioactivatable Derivatives of Inositol Polyphosphates andphosphoinositides,in Phosphoinositides: Chemistry, Biochemistry and Biomedical Applications, K. S. Bruzik, Ed. *Am. Chem. Soc., Symp. Ser.,* 718, 232–243 (1998)) inhibit calcium-mediated chloride secretion. D-myo-Inositol 1,4,5,6-tetrakisphosphate has been shown to inhibit a phosphatidylinositol PI-3 kinase ("PI-3 kinase") signaling pathway in colonic epithelia (Eckmann et al., *Proc. Natl. Acad. Sci. USA* 94:14456 (1997)). It has also recently been shown that 2,6-di-O-butyryl-myo-inositol 1,2, 4,5-octakis(acetoxylmethyl)ester increased the level of $Ca^{2+}$ in PC12 cells (C. Schultz et al. (1998), supra). U.S. Pat. No. 5,693,521 to Tsien et al. discloses the use of D-2,3-di-O-butyryl-myo-inositol 1,4,5,6-tetrakisphosphate octakis (acetoxymethyl)ester as a second messenger having enhanced cell permeability. International Publication No. WO 98/11901 by Traynor-Kaplan et al. describes various inositol phosphates with enhanced cell permeability that function as either agonists or antagonists of inositol polyphosphates. In addition, other inositol phosphates have been reported (S. Roemer et al., *J. Chem. Soc., Perkin Trans.* 1, 1683 (1996); International Publication No. WO 96/40695 to Tsien et al.; International Publication No. WO 98/11901 to A. Traynor-Kaplan et al.; Rudolf, M. T. et al., *Bioorg. & Med. Chem. Lett.,* 8:1857 (1998); Jiang, T. et al., *J. Biol. Chem.* 273:11017 (1998); Li, W., et al., *Tetrahedron* 53:12017 (1997)).

To the best of Applicants' knowledge, there has been no published report concerning the use of an inositol derivative for inhibiting the production of superoxide anion resulting from the inflammatory response. Citation or identification of any reference in Section 2 of this application is not an admission that such reference is available as prior art to the present invention.

3. SUMMARY OF THE INVENTION

The present invention encompasses novel compounds, useful for inhibiting superoxide anion production, having the general formula (I):

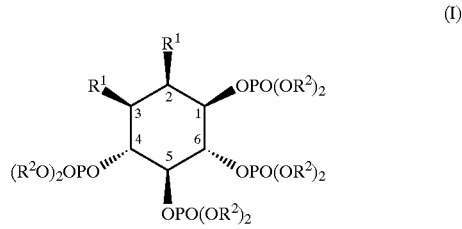

and racemates thereof, and pharmaceutically acceptable salts thereof, wherein each $R^1$ is independently selected from the group consisting of hydrogen, —OH, —$C_1$–$C_{20}$ straight or branched chain alkyl,—$C_2$–$C_{20}$ straight or branched chain alkenyl or alkynyl, —OC(O)$C_1$–$C_{20}$ straight or branched chain alkyl, —OC(O)$C_2$–$C_{20}$ straight or branched chain alkenyl or alkynyl, —O$C_1$–$C_{20}$ straight or branched chain alkyl, and —O$C_2$–$C_{20}$ straight or branched chain alkenyl or alknyl;

each $R^2$ is independently selected from the group consisting of hydrogen and —C($R^3$)($R^3$)OC(O)$C_1$–$C_4$ straight or branched chain alkyl; and each $R^3$ is independently selected from the group consisting of hydrogen, —$C_1$–$C_{12}$ alkyl, phenyl, and benzyl, or both $R^3$ taken together form a 5- or 6-membered ring, said $R^3$, except hydrogen, being unsubstituted or substituted with one or more halogen, —OH, $C_1$–$C_6$ alkyl, $NO_2$, —O$C_1$–$C_6$ alkyl, and —OC(O)$C_1$–$C_6$ alkyl groups;

with the proviso that the compound of formula (I) is not:

D- or D,L-myo-inositol 1,4,5,6-tetrakisphosphate;

D- or D,L-2,3-di-O-methyl-myo-inositol 1,4,5,6-tetrakisphosphate octakis(acetoxymethyl) ester;

D- or D,L-2-O-butyryl-3-O-methyl-myoinositol 1,4,5,6-tetrakisphosphate octakis(acetoxymethyl) ester;

D- or D,L-2-O-butyl-3-O-butyryl-myoinositol 1,4,5,6-tetrakisphosphate octakis(acetoxymethyl) ester;

D- or D,L-2,3-dideoxy-myo-inositol 1,4,5,6-tetrakisphosphate octakis(acetoxymethyl)ester, D- or D,L-2,3-di-O-butyl-myo-inositol 1,4,5,6-tetrakisphosphate octakis(acetoxymethyl) ester;

D- or D,L-3-O-buty1–2-O-butyryl-myo-inositol 1,4,5,6-tetrakisphosphate octakis(acetoxymethyl) ester;

D- or D,L-2,3-di-O-butyryl-myo-inositol 1,4,5,6-tetrakisphosphate octakis(acetoxymethyl) ester;

D- or D,L-3-O-butyryl-2-deoxy-myo-inositol 1,4,5,6-tetrakisphosphate octakis(acetoxymethyl) ester;

D,L-2-O-butyryl-1-deoxy-myo-inositol 3,4,5,6-tetrakisphosphate octakis(acetoxymethyl) ester;

D,L-1-O-butyryl-2-O-methyl-myo-inositol 3,4,5,6-tetrakisphosphate octakis(acetoxymethyl) ester; or D,L-1,2-cyclohexylidene-myo-inositol 1,4,5,6-tetrakisphosphate octakis(acetoxymethyl)ester.

The present invention further provides compositions, useful for the inhibition of superoxide anion production, comprising a therapeutically effective amount of compound of formula (I) or a racemate thereof, or a pharmaceutically acceptable salt thereof, with the proviso that the compound of formula (I) is not:

D- or DL-myo-inositol 1,4,5,6-tetrakisphosphate;

D- or D,L-2,3-di-O-methyl-myo-inositol 1,4,5,6-tetrakisphosphate octakis(acetoxymethyl) ester;

D- or D,L-2-O-butyryl-3-O-methyl-myo-inositol 1,4,5,6-tetrakisphosphate octakis(acetoxymethyl) ester;

D- or D,L-2-O-butyl-3-O-butyryl-myo-inositol 1,4,5,6-tetrakisphosphate octakis(acetoxymethyl) ester;

D- or D,L-2,3-dideoxy-myo-inositol 1,4,5,6-tetrakisphosphate octakis(acetoxymethyl)ester;

D- or D,L-2,3-di-O-butyl-myo-inositol 1,4,5,6-tetrakisphosphate octakis(acetoxymethyl) ester;

D- or D,L-3-O-butyl-2-O-butyryl-myo-inositol 1,4,5,6-tetrakisphosphate octakis(acetoxymethyl) ester;

D- or D,L-2,3-di-O-butyryl-myo-inositol 1,4,5,6-tetrakisphosphate octakis(acetoxymethyl) ester, D- or D,L-3-O-butyryl-2-deoxy-myo-inositol 1,4,5,6-tetrakisphosphate octakis(acetoxymethyl) ester;

D,L-2-O-butyryl-1-deoxy-myo-inositol 3,4,5,6-tetrakisphosphate octakis(acetoxymethyl) ester; or D,L-1 -O-butyTyl-2-O-methyl-myo-inositol 3,4,5,6-tetrakisphosphate octakis(acetoxymethyl) ester; or D,L-1,2-cyclohexylidene-myo-inositol 1,4,5,6-tetrakisphosphate octakis(acetoxymethyl)ester.

Such compositions can also comprise a pharmaceutically acceptable carrier or vehicle.

The invention further provides methods for inhibiting superoxide anion production, comprising administering to a patient in need of such inhibition a therapeutically effective amount of a compound of formula (I) or a racemate thereof, or a pharmaceutically acceptable salt thereof, wherein:

each $R^1$ is independently selected from the group consisting of hydrogen, —OH, —$C_1$–$C_{20}$ straight or branched chain alkyl, —$C_2$–$C_{20}$ straight or branched chain alkenyl or alkynyl, —OC(O)$C_1$–$C_{20}$ straight or branched chain alkyl, —OC(O)$C_2$–$C_{20}$ straight or branched chain alkenyl or alkynyl, —O$C_1$–$C_{20}$ straight or branched chain alkyl, and —O$C_2$–$C_{20}$ straight or branched chain alkenyl or alkynyl;

each $R^2$ is independently selected from the group consisting of hydrogen and —C($R^3$)($^3$)OC(O)$C_1$–$C_4$ straight or branched chain alkyl; and each $R^3$ is independently selected from the group consisting of hydrogen, —$C_1$–$C_{12}$ alkyl, phenyl, and benzyl, or both $R^3$ taken together form a 5- or 6-membered ring, said $R^3$, except hydrogen, being unsubstituted or substituted with one or more halogen, —OH, $C_1$–$C_6$ alky, $NO_2$, —O$C_1$–$C_6$ alkyl, and —OC(O)$C_1$–$C_6$ alkyl groups.

In one embodiment of the invention, the compound of formula (I) is administered in a composition comprising a pharmaceutically acceptable carrier or vehicle. Such carrier or vehicle can include a liposomal formulation.

The invention further provides methods for inhibiting superoxide anion production in a cell or tissue, comprising contacting the cell or tissue with an effective amount of a compound of formula (I) or a racemate thereof, or a pharmaceutically acceptable salt thereof, wherein:

each $R^1$ is independently selected from the group consisting of hydrogen, —OH, —$C_1$–$C_2$, straight or branched chain alkyl, —$C_2$–$C_{20}$ straight or branched chain alkenyl or alkynyl, —OC(O)$C_1$–$C_{20}$ straight or branched chain alkyl, —OC(O)$C_2$–$C_{20}$ straight or branched chain alkenyl or alkynyl, —OC—$C_{20}$ straight or branched chain alkyl, and —O$C_2$–$C_{20}$ straight or branched chain alkenyl or alkynyl;

each $R^2$ is independently selected from the group consisting of hydrogen and —C($^3$)($R^3$)OC(O)$C_1$–$C_4$ straight or branched chain alkyl; and each $R^3$ is independently selected from the group consisting of hydrogen, —$C_1$–$C_{12}$ alkyl, phenyl, and benzyl, or both $R^3$ taken together form a 5- or 6-membered ring, said $R^3$, except hydrogen, being unsubstituted or substituted with one or more halogen, —OH, $C_1$–$C_6$ alkyl, $NO_2$, —OC—$C_6$ alkyl, and —OC(O)$C_1$–$C_6$ alkyl groups.

In a preferred embodiment, the present methods comprise contacting a cell or tissue with a compound of formula (I) selected from the group consisting of:

D-myo-inositol ,4,5,6-tetrakisphosphate;

D-2,3-di-O-methyl-myo-inositol 1,4,5,6-tetrakisphosphate octakis(acetoxymethyl) ester;

D-2-O-butyry-3-O-methyl-myo-inositol 1,4,5,6-tetrakisphosphate octakis(acetoxymethyl) ester;

D-2-O-butyl-1,4,5,6-tetrakisphosphate octakis(acetoxymethyl) ester;

D-2,3-di-O-butyl-myo-inositol 1,4,5,6-tetrakisphosphate octakis(acetoxymethyl) ester;

D-3-O-butyl-2-O-butyryl-myo-inositol 1,4,5,6-tetrakisphosphate octakis(acetoxymethyl) ester;

D-2,3-di-O-butyryl-myo-inositol 1,4,5,6-tetrakisphosphate octakis(acetoxymethyl) ester; and D-3-O-butyry-2-deoxy-myo-inositol 1,4,5,6-tetrakisphosphate octakis(acetoxymethyl) ester, or a racemate thereof, or a pharmaceutically acceptable salt thereof.

In one embodiment of the invention, the compound of formula (I) contacts the cell or tissue in a composition comprising a pharmaceutically acceptable carrier or vehicle. The carrier or vehicle can include a liposomal formulation.

The present invention still further provides novel compounds, useful for inhibiting superoxide anion production, having the general formula (II):

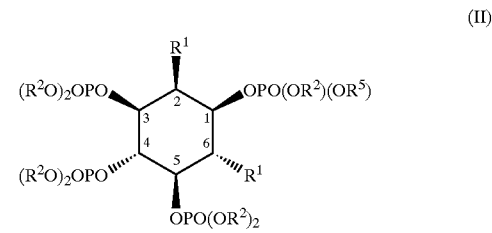

(II)

and L-enantiomers and racemates thereof, and pharmaceutically acceptable salts thereof, wherein each $R^1$ is independently selected from the group consisting of ydrogen, —OH, —$C_1$–$C_{20}$ straight or branched chain alkyl, —$C_2$–$C_{20}$ straight or branched chain lkenyl or alkynyl, —OC(O)$C_1$–$C_{20}$ straight or branched chain alkyl, —OC(O)$C_2$–$C_{20}$ straight or ranched chain alkenyl or alkynyl, —O$C_1$–$C_{20}$ straight or branched chain alkyl and —O$C_2$–$C_{20}$ traight or branched chain alkenyl or alkynyl;

each $R^2$ is independently selected from the group consisting of hydrogen and —C($^3$)($^3$)OC(O)$C_1$–$C_4$ straight or branched chain alkyl;

each $R^3$ is independently selected from the group consisting of hydrogen, —$C_1$–$C_{12}$ alkyl phenyl, and benzyn, or both $R^3$ taken together form a 5- or 6-membered ring, said $R^3$, except hydrogen, being unsubstituted or substituted with one or more halogen, —OH, $C_1$–$C_6$ alkyl $NO_2$, —O$C_1$–$C_6$ alkyl, and —OC(O)$C_1$–$C_6$ alkyl groups;

each $R^5$ is independently selected from the group consisting of hydrogen and —CH$_2$CH(XRW)CH$_2$XR$^6$;

each RW is independently selected from the group consisting of hydrogen, —C$_1$–C$_{23}$ straight or branched chain alkyl, —C$_2$–C$_{23}$ alkenyl and —C$_4$–C$_{23}$ alkadienyl; and each X is independently selected from the group consisting of —OC(O)—, —SC(O)—, —OC(S)—, —S— and —O—, with the proviso that the compound of formula (II) is not:

sn-di-O-palmitoyi-D,L-6-O-butyryl-phosphatidylinositol 3,4,5-trisphosphate heptakis(acetoxymethyl)ester;

sn-di-O-octanoyl-D,L-6-O-butyryl-phosphatidylinositol 3,4,5-trisphosphate heptakis(acetoxymethyl)ester;

sn-di-O-palmitoyl-D,L-2-O-butyryl-phosphatidylinositol 3,4,5-trisphosphate heptakis(acetoxymethyl)ester;

sn-di-O-octanoyl-D,L-2-O-butyryi-phospbatidylinositol 3,4,5-trisphosphate heptakis(acetoxymetbyl)ester;

sn-di-O-palmitoyl-D,L-2,6-di-O-butyryl-phosphatidylinositol 3,4,5-trisphosphate heptakis(acetoxymethyl)ester;

sn-di-O-octanoyl-D,L-2,6-di-O-butyryl-phosphatidylinositol 3,4,5-trisphosphate heptakis(acetoxymethyl)ester;

D- or D,L-phosphatidylinositol 3,4,5-trisphosphate;

sn-di-O-lauryl-D- or sn-di-O-lauryl-D,L-phosphatidylinositol 3,4,5-trisphosphate heptakis(acetoxymethyl)ester;

sn-di-O-octanoyl-D- or sn di-O-octanoyl-D,L-phosphatidylinositol 3,4,5-trisphosphate heptakis(acetoxymethyl)ester; or sn-di-O-palmitoyl-D- or sn-di-O-palmitoyl-D,L-phosphatidylinositol 3,4,5-trisphosphate heptakis(acetoxymethyl)ester.

The present invention further provides compositions, useful for the inhibition of superoxide anion production, comprising a therapeutically effective amount of compound of formula (II), or an L-enantiomer or racemate thereof, or a pharmaceutically acceptable salt thereof, with the proviso that the compound of formula (II) is not:

sn-di-O-palmitoyl-D,L-6-O-butyryl-phosphatidylinositol 3,4,5-trisphosphate heptakis(acetoxymethyl)ester;

sn-di-O-octanoyi-D,L-6-O-butyryl-phosphatidylinositol 3,4,5-trisphosphate heptakis(acetoxymethyl)ester;

sn-di-O-palmitoyl-D,L-2-O-butyryl-phosphatidylinositol 3,4,5-trisphosphate heptakis(acetoxymethyl)ester;

sn-di-O-octanoyl-D,L-2-O-butyryl-phosphatidylinositol 3,4,5-trisphosphate heptakis(acetoxymethyl)ester;

sn-di-O-palmitoyl-D,L-2,6-di-O-butyryl-phosphatidylinositol 3,4,5-trisphosphate heptakis(acetoxymethyl)ester;

sn-di-O-octanoyl-D,L-2,6-di-O-butyryl-phosphatidylinositol 3,4,5-trisphosphate heptakis(acetoxymethyl)ester;

D- or D,L-phosphatidylinositol 3,4,5-trisphosphate;

sn-di-O-lauyl-D- or sn-di-O-lauryl-D,L-phosphatidylinositol 3,4,5-trisphosphate heptakis(acetoxymethyl)ester;

sn-di-O-octanoyl-D- or sn-di-O-octanoyl-D,L-phosphatidylinositol 3,4,5-trisphosphate heptakis(acetoxymethyl)ester; or sn-di-O-palmitoyl-D- or sn-di-O-palmitoyl-D,L-phosphatidylinositol 3,4,5-trisphosphate heptakis(acetoxymethyl)ester.

The compositions can also comprise a pharmaceutically acceptable carrier or vehicle.

The invention furter provides methods for inhibiting superoxide anion production, comprising administering to a patient in need of such inhibition a therapeutically effective amount of a compound of formula (II), or an L-enantiomer, or a pharmaceutically acceptable salt thereof, wherein:

each $R^1$ is independently selected from the group consisting of hydrogen, —OH, —C$_1$–C$_{20}$ straight or branched chain alkyl, —C$_2$–C$_{20}$ straight or branched chain alkenyl or alkynyl, —OC(O)C$_1$–C$_{20}$ straight or branched chain alkyl, —OC(O)C$_2$–C$_{20}$ straight or branched chain alkenyl or alkynyl, —OC$_1$–C$_{20}$ straight or branched chain alkyl, and —OC$_2$–C$_{20}$ straight or branched chain alkenyl or alkynyl;

each $R^2$ is independently selected from the group consisting of hydrogen and —C(R$^3$)(R$^3$)OC(O)C$_1$–C$_4$ straight or branched chain alkyl;

each $R^3$ is independently selected from the group consisting of hydrogen, —C$_1$–C$_{12}$ alky, phenyl, and benzyl, or both $R^3$ taken together form a 5- or 6-membered ring, said $R^3$, except hydrogen, being unsubstituted or substituted with one or more halogen, —OH, C$_1$–C$_6$ alkyl, NO$_2$, —OC$_1$–C$_6$ alkyl, and —OC(O)C$_1$–C$_6$ alkyl groups;

each $R^5$ is independently selected from the group consisting of hydrogen and —CH$_2$CH(XR$^6$)CH$_2$XR$^6$;

each $R^6$ is independently selected from the group consisting of hydrogen, —C$_1$–C$_{23}$ straight or branched chain alkyl, —C$_2$–C$_{23}$ alkenyl and -C$_4$–C$_{23}$ alkadienyl; and each X is independently selected from the group consisting of —OC(O)—, —SC(O)—, —OC(S)—, —S— and —O—.

In a preferred embodiment, the present methods comprise administering to a patient a compound of formula (II) selected from the group consisting of:

sn-di-O-palmitoyl-D,L-6-O-butyryl-phosphatidylinositol 3,4,5-trisphosphate heptakis(acetoxymethyl)ester, or a D- or L-enantiomer thereof;

sn-di-O-octanoyl-D,L-6-O-butyryl-phosphatidylinositol 3,4,5-trisphosphate heptakis(acetoxymethyl)ester, or a D- or L-enantiomer thereof;

sn-di-O-palmitoyl-D,L-2-O-butyryl-phosphatidylinositol 3,4,5-trisphosphate heptakis(acetoxymethyl)ester, or a D- or L-enantiomer thereof;

sn-di-O-octanoyl-D,L-2-O-butyryl-phosphatidylinositol 3,4,5-trisphosphate heptakis(acetoxymethyl)ester, or a D- or L-enantiomer thereof;

sn-di-O-palmitoyl-D,L-2,6-di-O-butyryl-phosphatidylinositol 3,4,5-trisphosphate heptakis(acetoxymethyl)ester, or a D- or L-enantiomer thereof;

sn-di-O-octanoyl-D,L-2,6-di-O-butyryl-phosphatidylinositol 3,4,5-trisphosphate heptakis(acetoxymethyl)ester, or a D- or L-enantiomer thereof;

D-phosphatidylinositol 3,4,5-trisphosphate, or its corresponding L-enantiomer or racemate thereof;

di-O-lauryl-D-phosphatidylinositol 3,4,5-trisphosphate heptakis(acetoxymethyl)ester, or its corresponding L-enantiomer or racemate thereof; and di-O-octanoyl-D-phosphatidylinositol 3,4,5-trisphosphate heptakis(acetoxymethyl)ester, or its corresponding L-enantiomer or racemate thereof; and pharmaceutically acceptable salts thereof.

In one embodiment of the invention, the compound of formula (II) is administered in a composition comprising a pharmaceutically acceptable carrier or vehicle. The carrier or vehicle can include a liposomal formulation.

The invention further provides methods for inhibiting superoxide anion production in a cell or tissue, comprising contacting the cell or tissue with an effective amount of a compound of formula (II) or an L-enantiomer or a racemate thereof, or a pharmaceutically acceptable salt thereof wherein:

each $R^1$ is independently selected from the group consisting of hydrogen, —OH, —$C_1$–$C_{20}$ straight or branched chain alkyl, —$C_2$–$C_{20}$ straight or branched chain alkenyl or alkynyl, —OC(O)$C_1$–$C_{20}$ straight or branched chain alkyl, —OC(O)$C_2$–$C_{20}$ straight or branched chain alkenyl or alkynyl, —O$C_1$–$C_{20}$ straight or branched chain alkyl, and —O$C_2$–$C_{20}$ straight or branched chain alkenyl or alkynyl;

each $R^2$ is independently selected from the group consisting of hydrogen and —C($R^3$)($R^3$)OC(O)$C_1$–$C_4$ straight or branched chain alkyl;

each $R^3$ is independently selected from the group consisting of hydrogen, —$C_1$–$C_{12}$ alkyl, phenyl, and benzyl, or both $R^3$ taken together form a 5- or 6-membered ring, said $R^3$, except hydrogen, being unsubstituted or substituted with one or more halogen, —OH, $C_1$–$C_6$ alkyl, $NO_2$, —O$C_1$–$C_6$ alkyl, and —OC(O)$C_1$–$C_6$ alkyl groups;

each $R^5$ is independently selected from the group consisting of hydrogen and —$CH_2CH(W^6)CH_2XR^6$;

each $R^6$ is independently selected from the group consisting of hydrogen, —$C_1$–$C_{23}$ straight or branched chain alkyl, —$C_2$–$C_{23}$ alkenyl and —$C_4$–$C_{23}$ alkadienyl; and each X is independently selected from the group consisting of —OC(O)—, —SC(O)—, —OC(S)—, —S— and —O—.

In a preferred embodiment, the present methods comprise contacting a cell or tissue with a compound of formula (II) selected from the group consisting of:

sn-di-O-palmitoyl-D,L-6-O-butyryl-phosphatidylinositol 3,4,5-trisphosphate heptakis(acetoxymethyl)ester, or a D- or L-enantiomer thereof;

sn-di-O-octanoyl-D,L-6-O-butyryl-phosphatidylinositol 3,4,5-trisphosphate heptakis(acetoxyinethyl)ester, or a D- or L-enantiomer thereof;

sn-di-O-palmitoyl-D,L-2-O-butyryl-phosphatidylinositol 3,4,5-trisphosphate heptakis(acetoxymethyl)ester, or a D- or L-enantiomer thereof;

sn-di-O-octanoyl-D,L-2-O-butyryl-phosphatidylinositol 3,4,5-trisphosphate heptakis(acetoxymethyl)ester, or a D- or L-enantiomer thereof;

sn-di-O-palmitoyl-D,L-2,6-di-O-butyryl-phosphatidylinositol 3,4,5-trisphosphate heptakis(acetoxymethyl)ester, or a D- or L-enantiomer thereof;

sn-di-O-octanoyl-D,L-2,6-di-O-butyryl-phosphatidylinositol 3,4,5-trisphosphate heptakis(acetoxymethyl)ester, or a D- or L-enantiomer thereof;

D-phosphatidylinositol 3,4,5-trisphosphate, or its corresponding L-enantiomer or racemate thereof;

di-O4auryl-D-phosphatidylinositol 3,4,5-trisphosphate heptakis(acetoxymethyl)ester, or its corresponding L-enantiomer or racemate thereof;

di-O-octanoyl-D-phosphatidylinositol 3,4,5-trisphosphate heptakis(acetoxymethyl)ester, or its corresponding L-enantiomer or racemate thereof; and a pharmaceutically acceptable salt thereof.

In one embodiment of the invention, the compound of formula (II) contacts the cell or tissue in a composition comprising a pharmaceutically acceptable carrier or vehicle. Such carrier or vehicle can include a liposomal formulation.

The compounds of formulas (I) and (II) may be delivered by a variety of methods including orally, sublingually, intranasally, intramuscularly, intravenously, subcutaneously, intravaginally, transdermally, rectally, by inhalation, or as a mouthwash.

The present invention may be understood more fully by reference to the following figures, detailed description and illustrative examples which are intended to exemplify non-limiting embodiments of the invention.

4. DESCRIPTION OF THE FIGURES

FIG. 1 is a line graph showing a dose-dependent inhibition of superoxide anion production in human neutrophils by D-2,3-di-O-butyiyl-myo-inositol 1,4,5,6-tetrakisphosphate octakis(acetoxymethyl)ester. Data are represented as the mean ± the standard deviation of one experiment performed in quadruplicate, and is representative of three experiments.

Figure 2:
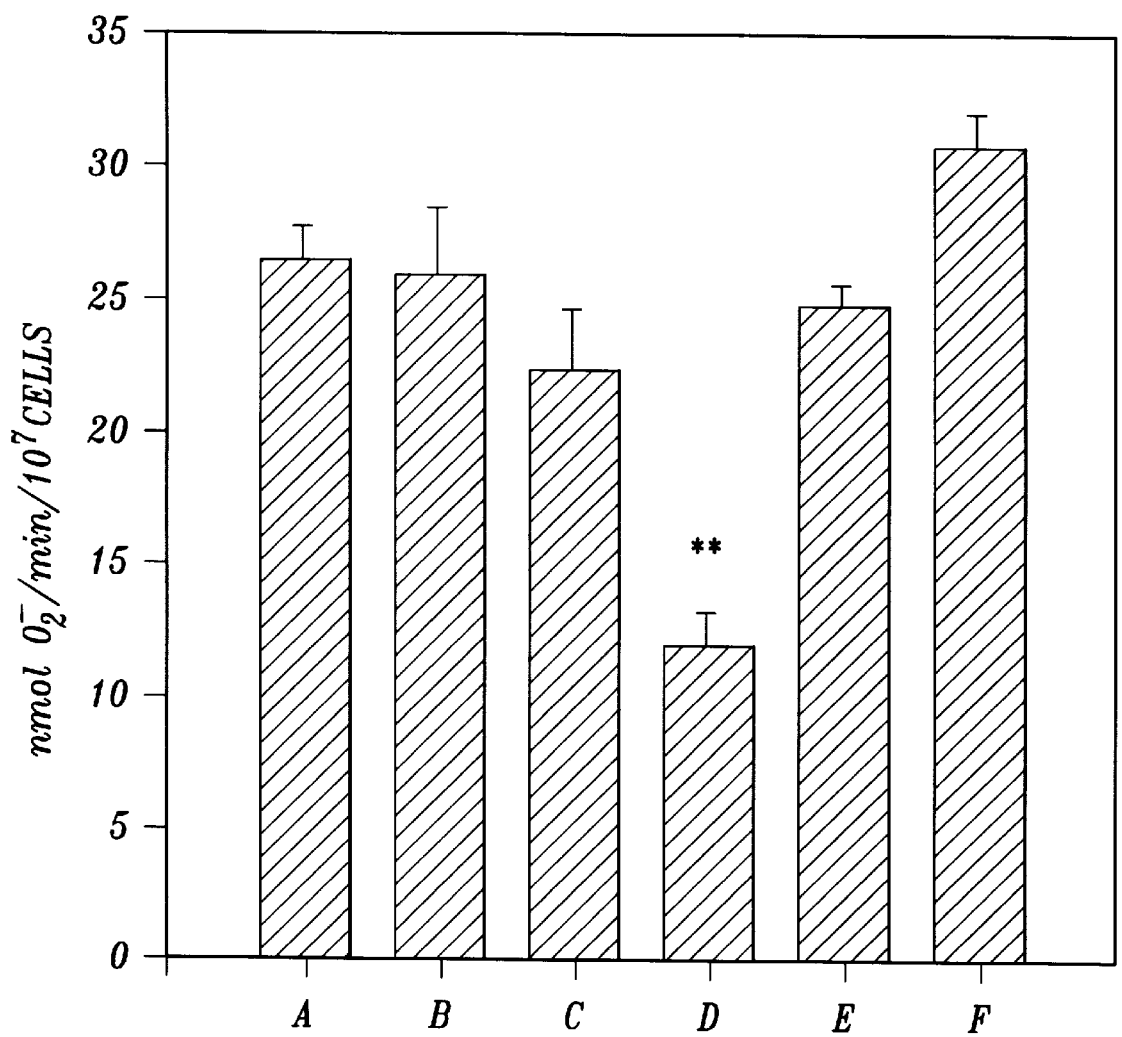

FIG. 2 is a bar graph showing the inhibitory effect of various inositol phosphates on superoxide anion production in human neutrophils. A, PBS; B, vehicle; C, D-1,2-di-O-butyiyl-myo-inositol 3,4,5,6-tetrakisphosphate octakis(acetoxymethyl)ester; D, D-2,3-di-O-butyryl-myo-inositol 1,4,5,6-tetrakisphosphate octakis(acetoxymethyl)ester; E, D-1,2-di-O-methyl-myo-inositol 3,4,5,6-tetrakisphosphate octakis(acetoxymethyl)ester; and F, D,L-1,2-di-O-butyryl-scyllo-inositol 3,4,5,6-tetrakisphosphate octakis(acetoxymethyl)ester. Data are represented as the mean ± the standard deviation of one experiment performed in quadruplicate. D vs. A, p<0.0002; D vs. B, p<0.003; D vs. C, p<0.007 Student's 2-tailed t-test.

Figure 3:
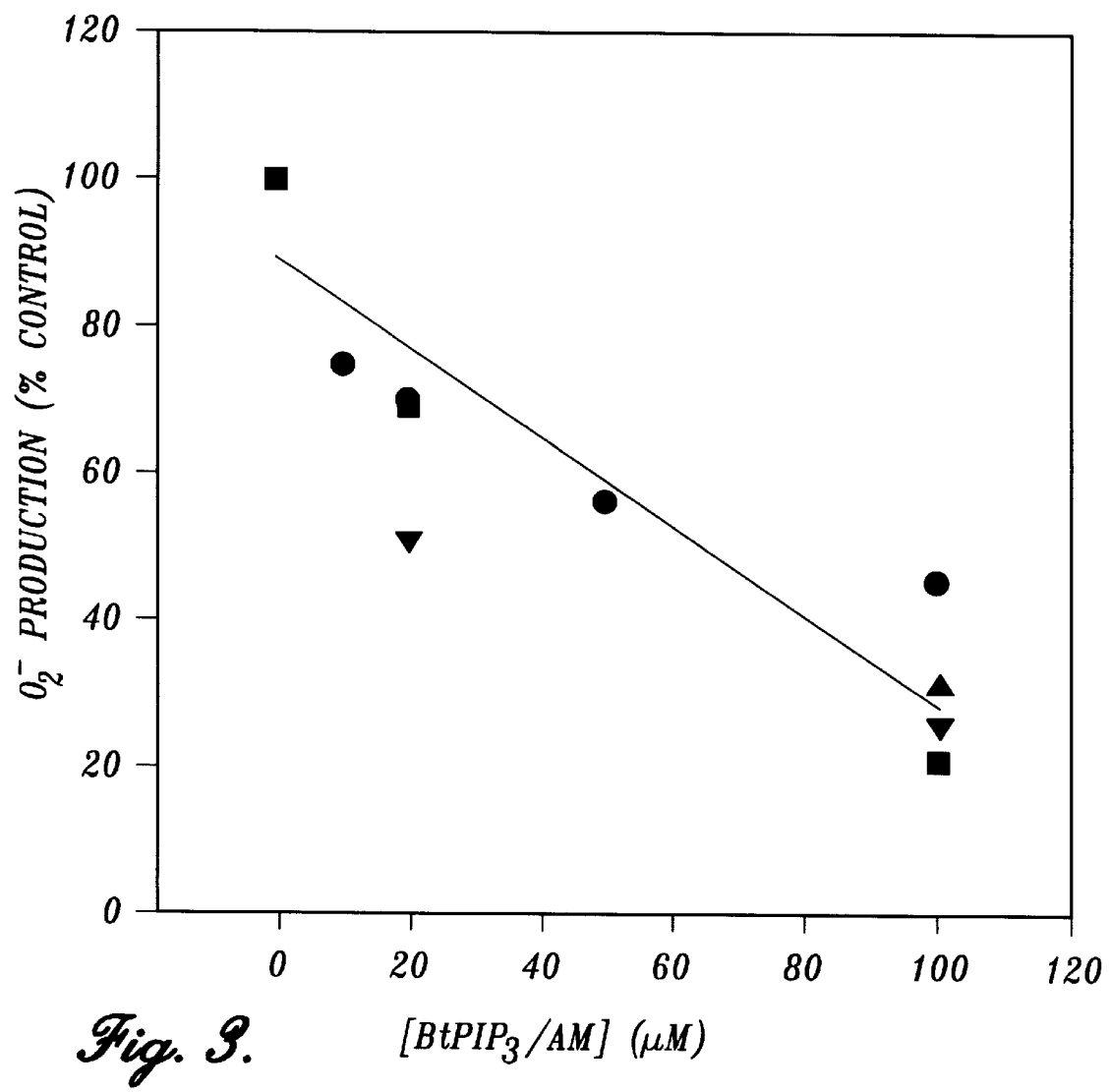

FIG. 3 is a line graph showing a dose-dependent inhibition of superoxide anion production in human neutrophils by sn-di-O-palmitoyl-D,L-6-O-butyryl-phosphatidylinositol 3,4,5-trisphosphate heptakis(acetoxymethyl)ester. The line represents first-order regression analysis. Data is expressed as percent control, and was calculated from values expressed as nmol/min/$10^7$ cells. The depicted data points are expressed as combined data from three separate experiments.

Figure 4:
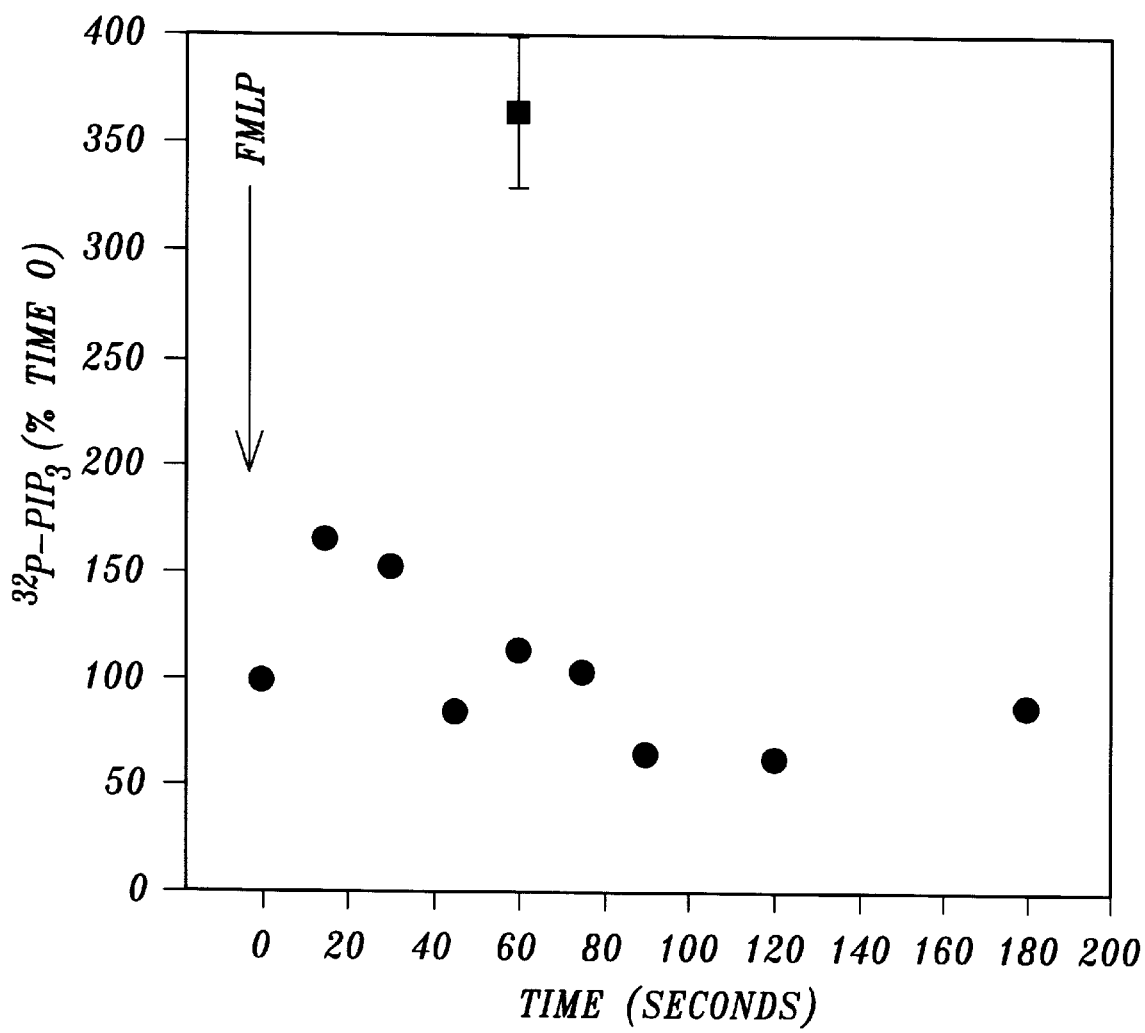

FIG. 4 is a time-course plot showing production of [$^{32}$P]-phosphatidylinositol 3,4,5-trisphosphate by f-methionine-leucine-phenylalanine-stimulated neutrophils prelabeled with $^{32}$P-orthophosphate as described previously (Traynor-Kaplan et al. (1988)) obtained from a Crohn's Disease patient. -●- signifies neutrophils from the Crohn's Disease patent; -■- signifies the control.

5. DETAILED DESCRIPTION OF THE INVENTION

5.1. Inositol Derivatives

In accordance with the present invention, the novel compounds usefuil for inhibiting superoxide anion production are represented by the general formula (I):

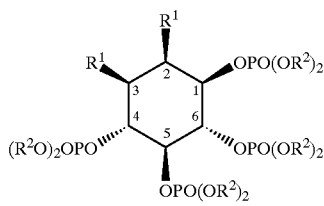

(I)

and racemates thereof, and pharmaceutically acceptable salts thereof, wherein each $R^1$ is independently selected from the group consisting of hydrogen, —OH, —$C_1$–$C_{20}$ straight or branched chain alkyl, —$C_2$–$C_{20}$ straight or branched chain alkenyl or alkynyl, —OC(O)$C_1$–$C_{20}$ straight or branched chain alkyl, —OC(O)$C_2$–$C_{20}$ straight or branched chain alkenyl or alkynyl, —O$C_1$–$C_{20}$ straight or branched chain alkyl, and —O$C_2$–$C_{20}$ straight or branched chain alkenyl or alkynyl;

each $R^2$ is independently selected from the group consisting of hydrogen and —C($R^3$)($R^3$)OC(O)$C_1$–$C_4$ straight or branched chain alkyl; and each $R^3$ is independently selected from the group consisting of hydrogen, —$C_1$–$C_{12}$ alkyl, phenyl, and benzyl, or both $R^3$ taken together form a 5- or 6-membered ring, said $R^3$, except hydrogen, being unsubstituted or substituted with one or more halogen, —OH, $C_1$–$C_6$ alkyl, $NO_2$, —O$C_1$–$C_6$ alky, and —OC(O)$C_1$–$C_6$ alkyl groups;

and by formula (II):

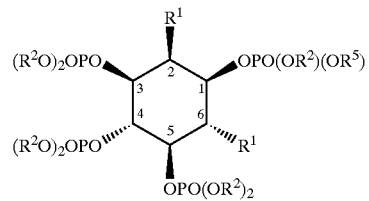

(II)

and L-enantiomers and racemates thereof, and pharmaceutically acceptable salts thereof, wherein each $R^1$ is independently selected from the group consisting of hydrogen, —OH, —$C_1$–$C_{20}$ straight or branched chain alkyl, —$C_2$–$C_{20}$ straight or branched chain alkenyl or alkynyl, —OC(O)$C_1$–$C_{20}$ straight or branched chain alkyl, —OC(O)$C_2$–$C_{20}$ straight or branched chain alkenyl or alkynyl, —O$C_1$–$C_{20}$ straight or branched chain alkyl, and —O$C_2$–$C_{20}$ straight or branched chain alkenyl or alkynyl;

each $R^2$ is independently selected from the group consisting of hydrogen and —C($R^3$)($R^3$)OC(O)$C_1$–$C_4$ straight or branched chain alkyl;

each $R^3$ is independently selected from the group consisting of hydrogen, —$C_1$–$C_{12}$ alkyl, phenyl, and benzyl, or both $R^3$ taken together form a 5- or 6-membered ring, said $R^3$, except hydrogen, being unsubstituted or substituted with one or more halogen, —OH, $C_1$–$C_6$ akyl, $NO_2$, —O$C_1$–$C_6$ alkyl, and —OC(O)$C_1$–$C_6$ alkyl groups;

each $R^5$ is independently selected from the group consisting of hydrogen and —$CH_2CH(XR^6)CH_2XR^6$;

each $R^6$ is independently selected from the group consisting of hydrogen, —$C_1$–$C_{23}$ straight or branched chain ally, —$C_2$–$C_{23}$ alkenyl and —$C_4$–$C_{23}$ alkadienyl; and each X is independently selected from the group consisting of —OC(O)—, —SC(O)—, —OC(S)—, —S— and —O—.

Where one or more $R^2$ groups is hydrogen, the compounds of formula (I) may exist in the form of a pharmaceutically acceptable salt. In addition, where $R^5$ or one or more $R^2$ groups are hydrogen, the compounds of formula (II) may exist in the form of a pharmaceutically acceptable salt. Useful pharmaceutically acceptable salts include sodium, potassium, lithium, calcium, magnesium, zinc, and iron salt.

The compounds of formula (I) and formula (II), and pharmaceutically acceptable salts thereof, are depicted in terms of their absolute stereochemistry, i.e., in the form of their D-enantiomers. But as contemplated herein, the compounds of formula (I) and pharmaceutically acceptable salts thereof are useful for inhibiting superoxide anion production caused by inflammation when also in the form of their racemates; the compounds of formula (II) and pharmaceutically acceptable salts thereof are useful for inhibiting superoxide anion production caused by inflammation when also in the form of their L-enantiomers and racemates. Preferably, the compounds of formula (I) and formula (II), and pharmaceutically acceptable salts thereof, are in the form of their D-enantiomers.

As used herein, the term "inositol derivatives" means, collectively, the compounds of formula (I) and racemates thereof, and pharmaceutically acceptable salts thereof, and the compounds of formula (II) and L-enantiomers and racemates thereof, and pharmaceutically acceptable salts thereof.

5.2. Synthesis of the Inositol Derivatives

The inositol derivatives can be obtained via conventional organic syntheses, e.g. as described below.

5.2.1. The Compounds OF Formula (I)

The compounds of formula (I) can be obtained as follows:

Where the compounds of formula (I) are desired as their D-enantiomer, D,L-1,4,5,6-tetra-O-benzyl-myoinositol can be resolved using (−)-camphanoyl chloride to obtain D-1,4,5,6-tetra-O-benzyl-myo-inositol as a starting material (Roemer et al., *J. Chem. Soc., Perkin Trans.* 1:1683 (1996)). Where the compounds of formula (I) are desired as racemates, D,L-1,4,5,6-tetra-O-benzyl-myo-inositol can be used as a starting material.

Where the groups at the 2- and 3-positions of the compound of formula (I) are to bear the same $R^1$ group, 1,4,5,6-tetra-O-benzyl-myo-inositol can be alkylated, alkenylated, alkynylated, or acylated by standard means to afford a D-1,4,5,6-tetra-O-benzyl-2,3-di-O-substituted-myo-inositol. Compounds of formula (I) wherein $R^1$ is —OH can be prepared, for example, by hydrolyzing a 2,3-cyclohexylidene-myo-inositol 1,4,5,6-tetrakisphosphate octakis(acyloxymethyl)ester, preferably at about pH 4.

Where the 3-position of the compound of formula (I) is to have an alkoxyl, alkenoxyl, or alkynoxyl group, and the 2-position of the compound of formula (I) is to have an acyl group or an alkoxyl, alkenoxyl, or alkynoxyl group different from that at the 3-position, 1,4,5,6-tetra-O-benzyl-myo-inositol (Roemer et al., supra) can be selectively alkylated, alkenylated, or alkynylated at the 3-position using dibutyltin oxide in the presence of the desired alkyl, alkenyl, or alkynyl halide. The resulting product can then be acylated, alkylated, alkenylated, or alkynylated by standard means to provide a 1,4,5,6-tetra-3-O-alkoxyl-O-benzyl-2-O-substituted-myo-inositol, a 1,4,5,6-tetra-3-O-alkenoxyl-O-benzyl-2-O-substituted-myo-inositol, or a 1,4,5,6-tetra-3-O-alkynoxyl-O-benzyl-2-O-substituted-myo-inositol.

Where the 2-position of the compound of formula (I) is to have an alkoxyl group, an alkenoxyl group, or an alkynoxyl group, and the 3-position of the compound of formula (I) is to have an acyl group, or an alkoxyl group, alkenoxyl group, or allnoxyl group different from that at the 2-position, 1,4,5,6-tetra-O-benzyl-myo-inositol can be selectively alkylated, alkenylated, or alkynylated at the 3-position with a protecting group, such as for example ap-methoxybenzyl protecting group, or an appropriate alkenoxyl or alkynoxyl group, to provide a 1,4,5,6-tetra-O-benzyl-3-O-p-methoxybenzyl-myo-inositol, 1,4,5,6-tetra-3-O-alkenoxyl-O-benzyl-myo-inositol, or 1,4,5,6-tetra-3-O-alkynoxyl-O-benzyl-myo-inositol. The 1,4,5,6-tetra-O-benzyl-3-O-p-methoxybenzyl-myo-inositol, 1,4,5,6-tetra-3-O-alkenoxyl-O-benzyl-myo-inositol, or 1,4,5,6-tetra-3-O-alkynoxyl-O-benzyl-myo-inositol can then be alkylated, alkenylated, or alkynylated at the 2-position using standard means; deprotected using DDQ; and then alkylated, alkenylated, alkynylated or acylated at the 3-position via standard means.

Compounds of formula (I) having intracellularly hydrolyzable esters at the 2- and 3-positions are preferred for administration to humans over compounds having —OH at these positions because the former are hydrolyzed more slowly and, accordingly, have a longer duration of action (Li et al., *Tetrahedron* 53:12017 (1997)). However, if the presence of a hydroxyl group is desired at the 2- or 3-position, it is preferrably protected by a protecting group such as triethylsilyl, which can then be removed by fluoride ion subsequent to adding the —PO(OR$^2$)$_2$ group.

Where the 2-position of the compound of formula (I) is to have a hydrogen atom, i.e., the compound of formula (I) is to be a 2-deoxyinositol derivative, its synthesis can begin with 1,4,5,6-tetra-O-benzyl-2-deoxy-myo-inositol (M. T. Rudolf et al.,*J. Med. Chem.* 41(19):3635–3644 (1998)). The 3-position of the 1,4,5,6-tetra-O-benzyl-2-deoxy-myo-inositol is then alkylated, alkenylated, alkynylated, or acylated as desired. Where the 2-position of the compound of formula (I) is to have a hydrogen atom, and the 3-position of the compound is to have a hydroxyl group, the hydroxyl group should first be protected using a protecting group such as triethylsilyl, which can then be removed by fluoride ion subsequent to adding the —PO(OR) group.

Where the 3-position of the compound of formula (I) is to have a hydrogen atom, i.e., the compound of formula (I) is to be a 3-deoxyinositol derivative, 1,4,5,6-tetra-O-benzyl-myo-inositol can be esterified at the 3-position with O-phenyl chlorothionofonnate; acylated, alkylated, alkenylated, or alkynylated at the 2-position as desired; and then reduced with tributyltin hydride to afford the 3-deoxyinositol derivative (M. T. Rudolf et al., supra). Where the 3-position of the compound of formula (I) is to have a hydrogen atom and the 2-position of the compound is to have a hydroxyl group, the hydroxyl group should first be protected using a protecting group such as triethylsilyl, which can then be removed by fluoride ion subsequent to adding the —PO(OR$^2$)$_2$ group.

The above tetrabenylinositols can be hydrogenolyzed using palladium on carbon (10%; preferably using 0.1 mole of palladium for each mole of benzyl group), and preferably in the presence of acetic acid, for several hours. The resulting deprotected inositols can then be treated with dibenzyl N,N-diethylphosphoramidite or dibenzyl N,N-diisopropylphosphoramidite in the presence of tetrazole, followed by treatment with peracetic acid (32% v/w) at −40° C., to afford, after work up, inositol tetrakis(dibenzyl) phosphates. The inositol tetrakis(dibenzyl)phosphates are then hydrogenolyzed, as described above for hydrogenolysis of the tetrabenzylinositols, to afford inositol tetrakisphosphates. Alkylation with Z—C(R$^3$)($^3$)OC(O)C$_1$–C$_4$ straight or branched chain alkyl, wherein Z is a leaving group, provides the compounds of formula (I) where R$^2$ is —C(R$^3$)($^3$)OC(O)C$_1$–C$_4$ straight or branched chain alkyl. The leaving group Z is any group whose departure will facilitate the formation of an ester bond between —C($^3$)($^3$)OC(O)C$_1$–C$_4$ straight or branched chain alkyl and a phosphate —OH group. Preferably, Z is halogen, C$_1$–C$_4$-C(O)O—, trifluoroacetate, methanesulfonate, trifluoromethanesulfonate, p-toluenesulfonate, 4-bromobenzenesulfonate and the like. Most preferably, Z—C($^3$)($^3$)OC(O)C$_1$–C$_4$ straight or branched chain alkyl is acetoxymethyl bromide, which is commercially available. Syntheses of butyroxymethyl bromide and propionoxymethyl bromide have also been described (Li et al., supra).

If compounds where the 2-position has a hydroxyl group, or compounds where the 3-position has a hydroxyl group, or compounds where both the 2- and 3-positions have hydroxyl groups are desired, the 2-position, the 3-position, or both the 2-position and the 3-position, respectively, should first be protected with protecting groups such as triethylsilyl. These protecting groups can then be removed by fluoride ion subsequent to adding the —PO(OR$^2$)$_2$ group.

In addition to the methods described above, the inositol derivatives can be prepared according to the methods of Roemer et al., *J. Chem. Soc., Perkin Trans.* 1:1683 (1996) and International Publication No. WO 98/26787 to Tsien et al.

Preferred compounds of formula (I) useful in the present methods can be obtained as follows:

D-2,3-di-O-methyl-myo-inositol 1,4,5,6-tetrakisphosphate octakis(acetoxymethyl) ester, D-2,3-di-O-butyryl-myo-inositol 1,4,5,6-tetrakisphosphate octakis(acetoxymethyl) ester, and D-2-O-butyryl-3-O-methyl-myo-inositol 1,4,5,6-tetrakisphosphate octakis (acetoxymethyl) ester can be obtained as described in S. Roemer et al. (*J. Chem. Soc., Perkin Trans.* 1:1683 (1996));

D-3-O-butyl-2-O-butyryl-myo-inositol 1,4,5,6-tetrakisphosphate octakis(acetoxymethyl) ester, D-3-O-butyryl-2-O-butyl-myo-inositol 1,4,5,6-tetrakisphosphate octakis(acetoxymethyl) ester, and D-2,3-di-O-butyl-myo-inositol 1,4,5,6-tetrakisphosphate octakis(acetoxymethyl) ester can be obtained as described in International Publication No. WO 98/11901 by Traynor-Kaplan et al.; and D-3-O-Buty -2-deoxy-myo-inositol 1,4,5,6-tetrakisphosphate octakis(acetoxymethyl) ester and D-2-O-butyryl-3-deoxy-myo-inositol 1,4,5,6 -tetrakisphosphate octakis(acetoxymethyl) ester can be obtained as described in M. T. Rudolf et al. (*J. Med. Chem.* 41(19):3635–3644 (1998)).

The compound D-myo-inositol 1,4,5,6-tetrakisphosphate can be synthesized by the methods of Roemer, et al. (*J. Chem. Soc., Perkin Trans.* 1:1683 (1996)).

The compounds of formula (I) in which one or more R$^2$ group is hydrogen can be synthesized from compounds of formula (I) wherein $R^2$ is —$C(R^3)(R^3)OC(O)C_1$–$C_4$ straight or branched chain alkyl using any agent known to those skilled in the art that can convert phosphate ester groups to phosphate hydroxyl groups. Alternatively, in order to generate the compounds of formula (I) in which one or more $R^2$ group is hydrogen, compounds of formula (I) wherein $R^2$ is —$C(R^3)(R^3)OC(O)C_1$–$C_4$ straight or branched chain alkyl can be hydrolyzed in vivo, intracellularly, by exposure to endogenous esterases.

Once the compounds of formula (I) have been synthesized, they can be purified or substantially purified, using conventional chromatography, recrystallization or other purification techniques known to those skilled in the art.

5.2.2. The Compounds of Formula (II)

The compounds of formula (II) can be obtained according to the general procedure of C. Schultz et al. ((1998), supra) as follows:

D- or D,L-3-O-Benzyl-1,2:4,5-di-O-cyclohexyliden-myo-inositol can be alkylated or acylated at the 6-position as desired, and then deketalized with acid to afford a 1-O-benzyl-6-O-substituted-myo-inositol. The 1-O-benzyl-6-O-substituted-myo-inositol is then converted to a 6-O-substituted-2,3,4,5-myo-inositol tetrakisphosphate via treatment with dibenzyl N,N-diethylphosphoramidite or dibenzyl N,N-diisopropylphosphoramidite, followed by hydrogenolysis as described above for the compounds of formula (I). The hydrogenolysis additionally removes the benzyl protecting group from the 1-hydroxyl group of the inositol derivative. The resulting tetrakisphosphate can be esterified with Z—$C(R^3)(R^3)OC(O)C_1$–$C_4$ straight or branched chain alkyl, preferably with acetoxymethyl bromide, in the presence of diisopropylethylamine, which affords a 6-O-substituted-1:2-cyclic-3,4,5-tetrakisphosphate heptakis(acetoxymethyl)ester with a cyclic phosphate group involving the 1- and 2-positions. Treatment of the 6-O-substituted-1:2-cyclic-3,4,5-tetrakisphosphate heptakis (acetoxymethyl)ester with $HOCH_2CH(XR^6)CH_2XR^6$, which can be obtained commercially or synthesized by methods well-known to those skilled in the art, affords the compounds of formula (II) where $R^1$ is —OH.

The synthesis of 6-substituted or 6-deoxy-6-alkyl inositol derivatives can be achieved by standard procedures, e.g., via a Swern oxidation of an otherwise fully-protected 6-hydroxy inositol derivative to its oxo-derivative and subsequent reaction with an alkyl Grignard reagent, followed by elimination of water. The resulting unsaturated product is hydrolyzed during the various, subsequent hydrogenation steps.

sn-di-O-Paimitoyl-D,L-6-O-butyryl-phosphatidylinositol 3,4,5-trisphosphate heptakis(acetoxymethyl)ester can be obtained according to the procedure described in C. Schultz et al. ((1998), supra).

The compound D-phosphatidylinositol 3,4,5-trisphosphate has been isolated from human cells (A. E. Traynor-Kaplan et al., *Nature* 334:353 (1988)).

The compounds of formula (II) wherein $R^5$ or one or more $R^2$ groups are hydrogen can be synthesized from compounds of formula (II) wherein $R^5$ is —$C(R^3)(R^3)OC(O)C_1$–$C_4$ straight or branched chain alkyl using any agent known to those skilled in the art that can convert phosphate ester groups to phosphate hydroxyl groups. Alternatively, in order to generate the compounds of formula (II) in which $R^5$ or one or more $R^2$ groups are hydrogen, the compounds of formula (11) wherein $R^5$ is —$C(R^3)(R^3)OC(O)C_1$–$C_4$ straight or branched chain alkyl can be hydrolyzed in vivo, intracellularly, by exposure to endogenous esterases.

Once the compounds of formula (II) have been synthesized, they can be purified or substantially purified, using conventional chromatography, recrystallization or other purification techniques known to those skilled in the art.

6. Methods For Use of the Inositol Derivatives

Due to the activity of the inositol derivatives of the present invention, the inositol derivatives are advantageously useful in veterinary and human medicine for inhibiting superoxide anion production and for reducing consequent tissue damage, as well as for treating or preventing pathological conditions including aging-related syndromes, carcinogenesis, multiple sclerosis, dementia, amyotropic lateral sclerosis, Parkinson's disease, Alzheimer's disease, and degenerative neuropathies. The inositol derivatives are useful for inhibiting superoxide anion production by neutrophils and macrophages in response to inflammation. Tissue-damaging superoxide anion is also produced in response to non-inflammatory conditions such as anoxia. Tissue damage resulting from anoxia includes, but is not limited to, brain damage suffered by stroke victims, particularly via reperfusion injury caused by reperfusion of blood to affected cerebral sites; heart muscle damage suffered by heart attack patients; cartilage and bone destruction suffered by rheumatoid arthritis patients; skin damage suffered by patients with acute or chronic dermatitis; and lung tissue damage, particularly to Type I alveolar epithelial cells, suffered by asthmatics and adult respiratory distress syndrome sufferers.

The inositol derivatives are useful for inhibiting superoxide anion production caused by allergic (reaginic) inflammation, e.g., inflammation associated with atopy, urticaria, anaphylaxis, asthma and seasonal rhinitis; inflammation mediated by cytotoxic antibodies, e.g., autoimmune hemolytic anemia, and thrombocytopenia associated with systemic lupus erythematosus; inflammation mediated by immune complexes, e.g., rheumatoid arthritis and systemic lupus erythematosus; and inflammation mediated by mononuclear leukocytes, e.g., granulomatosis diseases, tuberculosis, leprosy and sarcoidosis.

The inositol derivatives are also useful for inhibiting superoxide anion production caused by inflammation accompanying an acute or chronic condition including, but not limited to, physical trauma, e.g., that resulting from surgery, natural childbirth, or other physical injury; dermatitis, e.g., eczema, psoriasis, acute contact dermatitis or drug eruption; gastritis; inflammatory bowel disease; rheumatoid arthritis; non-rheumatoid arthritis; asthma; ischemia/reperfusion injury; ulcerative colitis; adult respiratory distress syndrome caused by sepsis, traumatic injury, bone fracture, hypertransfusion, aspiration of gastric contents, pancreatitis or skin burns; non-asthma lung diseases such as idiopathic pulmonary fibrosis (fibrosing alveolitis), hypersensitivity pneumonitis, sarcoidosis, and granulomatous vasculitides; smoke inhalation; heart attack; stroke; chronic lung disease; arthritis; alcoholic liver disease; xenobiotic toxicity; and iron toxicity (collectively, "inflammation-accompanying conditions.")

Many non-immune cells such as vascular smooth muscle cells, pulmonary arterial smooth muscle cells, and human epidermoid carcinoma cells generate superoxide anion at 1000-fold lower levels than do neutrophils or macrophages. In these cases, the generation of superoxide anion appears to play a role in signal transduction rather than in inflammation (Sundaresan et al., *Science* 270:296–9 (1995); Zhang et al.,

*Am J. Respir. Cell. Mol. Biol.* 19:324–32 (1998); Bae et al., *J. Biol. Chem.* 272:217–21 (1997)). But even at these low levels, the superoxide anion generated from non-immune cells can lead to pathological conditions described above. Accordingly, the inositol derivatives are useful for treating and preventing the inflammation-accompanying conditions above.

When administered to a patient, e.g., a mammal for veterinary use or to a human for clinical use, or when made to contact a cell or tissue, the inositol derivatives are preferably in isolated form. By "isolated" is meant that prior to administration, the inositol derivatives are separated from other components of a synthetic organic chemical reaction mixture. Preferably, the inositol derivatives are purified via conventional techniques.

When administered to a patient, e.g., a mammal for veterinary use or to a human for clinical use, or when made to contact a cell or tissue, the inositol derivatives can be used alone or in combination with any physiologically acceptable carrier or vehicle suitable for enteral or parenteral delivery. Where used for enteral, parenteral, topical, otic, opthalmalogic, intranasal, oral, sublingual, intramuscular, intravenous, subcutaneous, intravaginal, transdermal, or rectal administration, the physiologically acceptable carrier or vehicle should be sterile and suitable for in vivo use in a human, or for use in a veterinary clinical situation.

In addition, the inositol derivatives can be administered to patients or contacted with a cell or tissue in liposome formulations, which facilitate their passage through cell membranes. Accordingly, the relative impermeability of cell membranes to relatively polar inositol derivatives can be overcome by their encapsulation in liposomal formulations. The characteristics of liposomes can be manipulated by methods known to those of ordinary skill in the art, such that size, membrane fluidity, tissue targeting, and compound release kinetics are adapted to the particular tissue-damaging condition (Georgiadis, *NIPS* 4:146 (1989)). Liposomes of various sizes and compositions that encapsulate the inositol derivatives for delivery can be achieved by methods known to those skilled in the art (See, for example, Hope et al., *Biochim. Biophys. Acta* 812:55 (1985); Hernandez, et al., *J. Microencapsul.* 4:315 (1987); Singh, et al., *Cancer Lett.* 84:15 (1994); and Dipali, et al., *J. Pharn. Pharmacol.* 48:1112 (1996)).

The compounds of formula (I) wherein one or more $R^2$ is hydrogen, particularly D-myo-inositol 1,4,5,6-tetrakisphosphate, as well as the compounds of formula (II) wherein $R^5$ or one or more $R^2$ groups are hydrogen, particularly D-phosphatidylinositol 3,4,5-trisphosphate, are especially useful for inhibiting superoxide anion production when administered to a patient or contacted with a cell or tissue in a liposomal formulation.

The inositol derivatives can also be administered in the form of a pharmaceutical preparation, for example, in solid, semisolid or liquid form, that contains at least one of the inositol derivatives of the present invention as a bioactive component, alone or in combination with an anti-inflammatory compound, in admixture with a carrier, vehicle or an excipient suitable for enteral or parental delivery. Anti-inflammatory compounds useful in this regard include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, colchicine, allopurinol, probenecid, sulfinpyrazone and benzbromarone.

In addition, the inositol derivatives of the present invention may be compounded, for example, with a pharmaceutically acceptable carrier or vehicle for solid compositions such as tablets, pellets or capsules; capsules containing liquids; suppositories; solutions; emulsions; aerosols; sprays; suspensions or any other form suitable for use. Suitable carriers and vehicles include, for example, sterile water, sterile physiological saline, gum acacia, gelatin, starch paste, talc, keratin, colloidal silica, urea and the like. In addition, auxiliary, stabilizing, thickening, lubricating and coloring agents may be used. The inositol derivatives are present in the compositions in a therapeutically effective amount, i.e., an amount sufficient to inhibit superoxide anion production.

The compositions of the present invention may be delivered by a variety of methods including orally, sublingually, intranasally, intramuscularly, intravenously, subcutaneously, intravaginally, transdermally, rectally, by inhalation, as a mouthwash, or topically to the inside of the ears, nose, or eyes. The preferred mode of delivery is left to the discretion of the practitioner, and will depend in-part upon the site of superoxide anion production.

For example, where the inflammation results from adult respiratory distress syndrome, asthma, or another acute or chronic inflammatory condition of the lungs, the inositol derivatives can be delivered as an atomized aerosol, via a nebulizer, or via perfusion in a fluorocarbon or synthetic pulmonary surfactant; alternatively, the inositol derivatives can be delivered intravenously directly to circulating neutrophils or macrophages.

Where the inflammation results from dermatitis, the inositol derivatives can be delivered topically in a shampoo, cream, ointment, lotion or salve base. For example, where the inflammation results from psoriasis, a topical composition can be administered to the affected area. An illustrative composition consists of a Part A that is heated to 75° C. and contains 2 g polyoxyethylene (40) stearate, 1 g polyoxyethylene (20), 1 g sorbitan monooleate, 4 g glycerol monostearate, 2 g beeswax, 3 g cetyl alcohol, and 1 g isopropyl myristate; and of a Part B that is heated to 80° C. and contains 76 ml water, 5 ml propylene glycol, 0.5 g carbomer 934. Part B is added slowly to Part A with mixing. A therapeutically effective amount, for example, about 0.001 mg/kg to about 100 mg/kg body weight, of an inositol derivative is added to the resulting mixture, which is allowed to cool to room temperature. The above-prepared composition can be topically delivered twice daily for a week to a patient at the site of the patient's psoriasis. As a result of the delivery, the patient has a reduced level of superoxide anion production and a reduced level of consequent tissue damage caused by inflammation resulting from the psoriasis.

Where the inflammation results from gastritis, ulcerative colitis or inflammatory bowel disease, a composition comprising a physiologically acceptable carrier or vehicle and a therapeutically effective amount of an inositol derivative can be delivered rectally once daily for one week, in the form of an enema or suppository, or orally in the form of a tablet or capsule formulated to prevent dissolution prior to entry into the afflicted portion of the gastrointestinal tract; where the inflammation results from childbirth, the inositol derivatives can be delivered intravaginally, in the form of a douche; where the inflammation results from oral surgery, the inositol derivatives can be delivered in the form of a mouthwash; where the inflammation results from eye injury, the inositol can be delivered in the form of an eye wash. As a result of the delivery, the patient has a reduced level of superoxide anion production and a reduced level of consequent tissue damage caused by inflammation resulting from any of these conditions.

Where the inflammation results from arthritis, the inositol derivatives can be delivered parenterally via injection directly into the synovial fluid or systemically via i.v., optionally in a liposome formulation designed to target specific sites of superoxide anion production, or topically in a lipophilic base. This type of liposome formulation can comprise liposomes having surface molecules that allow the liposomes to adhere to an inflammatory site or a neutrophil. The liposomes can also contain antibodies to the leukocyte cell surface antigen, C18. The liposome formulation can additionally comprise phosphatidyl serine, which, when present on the cell surface, signals that the cell is undergoing apoptosis and stimulates neutrophil chemotaxis.

Where the inflammation results from heart attack, a composition comprising physiological saline and a therapeutically effective amount of an inositol derivative can be delivered intravenously to a patient within 24–48 hours, and preferably within 12 hours, following the heart attack; via injection into a vein leading directly to the heart; or into the heart muscle itself. As a result of the delivery, the patient has a reduced level of superoxide anion production and a reduced level of consequent tissue damage caused by inflammation resulting from the heart attack.

Where the inflammation results from a stroke, a composition comprising physiological saline and a therapeutically effective amount of an inositol derivative can be delivered via i.v. or, depending upon the site of the lesion, via direct injection into the cerebral spinal fluid of a patient within 6 hours of suffering a stroke. Preferably, the inositol derivatives are injected into a blood vessel leading directly to the afflicted site. Optionally, the inositol derivatives can be delivered in a liposome formulation, such as described above.

As a result of the delivery, the patient has a reduced level of superoxide anion production and a reduced level of consequent tissue damage caused by inflammation resulting from the stroke.

Compositions for oral delivery may be in the form of tablets, troches, lozenges, aqueous or oily suspensions, granules or powders, emulsions, capsules, syrups or elixirs. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, compositions in tablet form may be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used.

Aqueous suspensions containing the inositol derivatives may also contain one or more preservatives, such as, for example, ethyl or n-propyl-p-hydroxy-benzoate, one or more coloring agents, flavoring agents or sweetening agents.

Because the inositol derivatives can exist in the form of phosphate esters, and because the inositol derivatives can contain alky, alkenyl, alkynyl or acyl groups, the inositol derivatives can possess enhanced lipophilic properties, which allow for passive diffusion across plasma membranes. This design permits the inositol derivatives to more easily penetrate cell membranes and travel to sites having a significant superoxide anion concentration more easily and quickly.

Without being bound by any particular theory, it is believed that the inositol derivatives, some of which contain phosphate esters, function as "prodrugs" of a metabolized form of the inositol derivatives, in which one or more of the phosphate esters are hydrolyzed. The hydrolyzed form of these prodrugs may be the actual pharmacological agent responsible for the inhibition of superoxide anion production. Metabolized forms of inositol derivatives that are active, or whose metabolites are active, most likely include the fully hydrolyzed compounds inositol 1,4,5,6-tetrakisphosphate and phosphatidylinositol 3,4,5-trisphosphate, as well as partially hydrolyzed inositol compounds. The prodrugs, by virtue of their being more lipophilic than the actual pharmacological agents themselves, can easily penetrate plasma membranes. Once within a site of relatively high superoxide anion concentration, such as a site of inflammation, the prodrugs are converted, generally enzymatically, to the active pharmacological agent. In addition, because in vivo conversion of a prodrug to its active pharmacological form generally occurs over a period of time, rather than instantaneously, the use of prodrugs offers the patient or subject the benefit of a sustained release of the pharmacological agent which generally results in a longer duration of action.

Accordingly, the inositol derivatives are particularly useful for inhibiting superoxide anion production caused by inflammation of the brain, e.g., as a result of stroke. For pharmacological agents to enter brain tissue in therapeutically effective concentrations, the blood-brain barrier—a network of tightly joined endothelial cells of central nervous system capillaries—must first be penetrated. Because the membranes of the endothelial cells are phospholipoidal in nature, pharmacological agents that are lipophilic in nature are better able to diffuse through the blood-brain barrier than those that are not (see Marcus E. Brewster et al., *Chemical Approaches to Brain-Targeting of Biologically Active Compounds*, in Drug Design for Neuroscience 435–67 (Alan P. Kozikowski ed., Raven Press, Ltd. 1993)). By virtue of their phosphate ester groups, the inositol derivatives are able to transverse the blood-brain barrier more easily than other drugs.

In addition, without being bound by any particular theory, it is believed that the inositol derivatives, by virtue of the fact that they comprise phosphate ester groups, are able to accumulate within "depots," i.e., fatty domains of the brain, in particular, within cell membranes. Within in such depots, the inositol derivatives act to inhibit superoxide anion production caused by inflammation.

In a further embodiment, the present invention contemplates the use of an inositol derivative when delivered at a dose of about 0.001 mg/kg to about 100 mg/kg body weight, preferably from about 0.01 to about 10 mg/kg body weight. The inositol derivatives can be delivered up to several times per day, as needed. Treatment can be continued, for example, until the inflammation has subsided, or until the malady causing the inflammation has been cured or has abated. The appropriate dosage of the compositions can be readily determined by the skilled medical practitioner.

For the inhibition of superoxide anion production resulting from an inflammation-accompanying condition described above, a composition of the present invention may be administered to a patient or delivered to a cell or tissue that contains an inositol derivative together with an agent useful for the treatment of that inflammation-accompanying condition. For example, for the treatment of dermatitis, such an agent can be tretinoin, isotretinoin, etretinate, β-carotene, cyclosporine, 4,4'-diaminodiphenylsulfone, calcipotriene, anthralin, methoxsalen, trioxalen, coal tar, an α-hydroxyacid or colchicine; for the treatment of gastritis, such an agent can be sucralfate, cimetidine, ranitidine, famotidine, nizatidine or an antacid; for the treatment of inflammatory bowel disease or ulcerative colitis, such an agent can be mesalamine, olsalazine, sulfasalazine, hydrocortisone or prednisone; for the treatment of rheumatoid arthritis, such an agent can be apazone, cyclophosphamaide, cyclosporine, diclofenac, etodolac, mefanamic acid, meclofenamate sodium, cyclosporine, azathioprine, methotrexate, prednisone, triamcinolone acetonide, penicillamine, hydroxychloroquine, methotrexate, sulindac or a salicylate; for the treatment of asthma or adult respiratory distress syndrome, such an agent can be cyclosporine, a belladonna alkaloid, beclomethasone dipropionate, triamcinolone acetonide, flunisolide, budesonide, cromolyn, nedocromil, albuterol, bitolterol mesylate, pirbuterol, salmeterol, terbutaline or theophylline; for the treatment of heart attack, such an agent can be isoproterenol; and for stroke, such an agent can be methylprednisolone or tirilazad mesylate.

Alternatively, the compositions comprising an inositol derivative can be delivered in combination with, prior to, concurrent with or subsequent to the delivery of another agent useful for the treatment of that inflammation-accompanying condition, as described above.

In addition, the inositol derivatives can be used for research purposes, for example, to investigate the mechanism and activity of other agents thought to be useful for inhibiting superoxide anion production.

The following examples are set forth to assist in understanding the invention and should not, of course, be construed as specifically limiting the invention described and claimed herein. Such variations of the invention which would be within the purview of those in the art, including the substitution of all equivalents now known or later developed, including changes in formulation or minor changes in experimental design, are to be considered to fall within the scope of the invention incorporated herein.

6. Methods For Use of the Inositol Derivatives -Tetrakisphosphate Octakis(Acetoxymethyl)Ester Human neutrophils were isolated from whole blood as described by Badway et al. (*Biochem. Biophys. Res. Commun.* 106:170 (1982)). The rate of production of superoxide by intact human neutrophils isolated from whole blood was determined at 37° C. in a Thermomax kinetic microplate reader equipped with a 550 (+/−1) nm filter obtained from Molecular Devices Corp., Menlo Park, Calif., as previously described by L. A. Mayo et al. (*Enzymol.* 186:567 (1990)).

In this assay (total volume 0.25 mL), cytochrome C reduction in a pair of reaction vessels, one of which contained 15 μg of superoxide dismutase ("SOD"), was continuously measured at 550 nm after stimulation of the neutrophil suspension with a 1 μM solution of the formyl peptide f-methionine-leucine-phenylalanine ("f-MetLeuPhe"), which signals macrophages and neutrophils to produce inositol phosphate derivatives. Maximum reaction velocities were determined using SoftMax kinetic analysis software (Moleuclar Devices, Menlo Park, Calif.). The rate of superoxide production, inhibitable by SOD, was calculated by subtracting the velocity of cytochrome C reduction in the SOD-containing reaction mixture from that of the reaction mixture in which the SOD was absent. Absorbance changes were converted to nanomoles of superoxide anion as described previously for the 550 nm filter (Mayo et al. (1990), supra).

Neutrophils were incubated in phosphate-buffered saline ("PBS") at a density of $10^7$/mL at 37° C. in the presence of various concentrations including 50, 100, 200 and 400 micromolar of either D-2,3-di-O-butyryl-myo-inositol 1,4,5,6-tetrakisphosphate octakis(acetoxymethyl)ester or D-1,2-di-O-butyryl-myo-inositol 3,4,5,6-tetrakisphosphate octakis (acetoxymethyl)ester. Cells were briefly placed on ice prior to the measurement of superoxide anion production. Superoxide anion production was expressed as a percentage of the maximal rate of cytochrome C reduction observed with control neutrophils preincubated for thirty minutes with vehicle (dimethylsulfoxide/5% pluronic detergent, Lutrol F127, BASF, Germany). Blanking wells containing 60 micrograms/ml of superoxide dismutase were run simultaneously with test reactions and maximum velocity measurements for these control reactions were subtracted from test well values to provide the SOD-inhibitable velocity component of each experimental well. The rate of maximum absorbance change was converted to nanomoles of superoxide per minute. The control rate of superoxide anion production was 27.15±4.56 nmol superoxide anion/min/$10^7$ cells.

As shown in FIG. 1, treatment of human neutrophils with D-2,3-di-O-butyryl-myo-inositol 1,4,5,6-tetrakisphosphate octakis(acetoxymethyl)ester for thirty minutes prior to neutrophil stimulation inhibited subsequent f-MetLeuPhe-stimulated superoxide production in human neutrophils in a dose-dependent manner.

FIG. 2 illustrates the stereo-selectivity of D-2,3-di-O-butyryl-myo-inositol 1,4,5,6-tetrakisphosphate octakis (acetoxymethyl)ester in its ability to inhibit f-MetLeuPhe-stimulated superoxide production in human neutrophils. In this experiment, neutrophils were stimulated with f-MetLeuPhe as described above, and treated with 200 μM of either:

A, PBS;

B, vehicle;

C, D-1,2-di-O-butyryl-myo-inositol 3,4,5,6-tetrakisphosphate octakis(acetoxymethyl)ester, the enantiomer of D-2,3-di-O-butyryl-myo-inositol 1,4,5, 6-tetrakisphosphate octakis(acetoxymethyl)ester;

D, D-2,3-di-O-butyryl-myo-inositol 1,4,5,6-tetrakisphosphate octakis(acetoxymethyl)ester;

E, D-1,2-di-O-methyl-myo-inositol 3,4,5,6-tetrakisphosphate octakis(acetoxymethyl)ester; or F, D,L-1,2-di-O-butyryl-scyllo-inositol 3,4,5,6-tetrakisphosphate octakis(acetoxymethyl)ester.

That the inhibitory effect of D-2,3-di-O-butyryl-myo-inositol 1,4,5,6-tetrakisphosphate octakis(acetoxymethyl) ester is selective with respect to structural changes is illustrated by the fact that neither D-1,2-di-O-methyl-myo-inositol 3,4,5,6-tetrakisphosphate octakis(acetoxymethyl) ester nor D,L-1,2-di-O-butyryl-scyllo-inositol 3,4,5,6-tetrakisphosphate octakis(acetoxymethyl)ester, a structural isomer of D-2,3-di-O-butyryl-myo-inositol 1,4,5,6-tetrakisphospate octakis (acetoxymethyl)ester, inhibits superoxide anion production. That the inhibitory effect of D-2,3-di-O-butyryl-myo-inositol 1,4,5,6-tetrakisphosphate octakis(acetoxymethyl)ester is enantioselective is illustrated by the fact that D-1,2-di-O-butyryl-myo-inositol 3,4,5,6-tetrakisphosphate octakis(acetoxymethyl)ester, which is equivalent to the L-enantiomer of D-2,3-di-O-butyryl-myo-inositol 1,4,5,6-tetrakisphosphate octakis(acetoxymethyl) ester, does not inhibit superoxide anion production to a significant degree.

These results demonstrate that D-2,3-di-O-butyryl-myo-inositol 1,4,5,6-tetrakisphosphate octakis(acetoxymethyl) ester, an illustrative compound of formula (I), is effective at inhibiting superoxide anion production in human neutrophils and useful for inhibiting tissue damage caused by superoxide anion production.

6. Methods For Use of the Inositol Derivatives

Inhibition of f-Methionine-Leucine-Phenylalanine-Stimulated Superoxide Anion Production in Human Neutrophils by sn-di-O -Palmitoyl D,L6-O-Butyryl-Prosphatidylinositol 3,4,5-Trisprosphate Heptakis(Acetoxymethyl)Ester The same experimental protocol of Example 7, above, was used with the following exceptions: Polymorphonuclear leucocytes ("PMNs") isolated from human blood were preincubated with sn-di-O-palmitoyl-D,L-6-O-butyryl-phosphatidylinositol 3,4,5-trisphosphate heptakis (acetoxymethyl)ester for ten minutes prior to addition of f-MetLeuPhe stimulus and measurement of subsequent superoxide anion production. Control aliquots were incubated with vehicle (dimethylsulfoxide/5% pluronic detergent, Lutrol F127, BASF, Germany) for ten minutes, and ranged in concentration from 19.6–35.4 nmol superoxide anion/$10^7$ cells.

sn-Di-O-palmitoyl-D,L-6-O-butyryl-phosphatidylinositol 3,4,5-trisphosphate heptakis(acetoxymethyl)ester inhibits generation of superoxide anion from human PMNs. As shown in FIG. 3, the inhibitory effect of sn-di-O-palmitoyl-D,L-6-O-butyryl-phosphatidylinositol 3,4,5-trisphosphate heptakis(acetoxyrnethyl)ester is dose-dependent at extracellular concentrations of $10^{-5}$ to $10^{-4}$ M. Comparable dose-dependent results were also obtained where the PMNs were incubated with sn-di-O-palmitoyl-D,L-6-O-butyryl-phosphatidylinositol 3,4,5-trisphosphate heptakis (acetoxymethyl)ester from ten to thirty minutes prior to f-MetLeuPhe stimulation. These results indicate that sn-di-O-palmitoyl-D,L-6-O-butyryl-phosphatidylinositol 3,4,5-trisphosphate heptakis(acetoxymethyl)ester, an illustrative compound of formula (II), is effective at inhibiting superoxide anion production by PMNs, and is useful for inhibiting tissue damage caused by superoxide anion production.

9. EXAMPLE

Inhibition of f-Methionine-Leucine-Phenylalanine-Stimulated Superoxide Anion Production in Human Neutrophils by D-2,3-di-O-Butyryl-Myo-Inositol 1,4,5,6-Tetrakisphosphate Octakis(Acetoxymethyl)Ester and D-2,3-di-O-Butyryl-Myo-Inositol 1,4,5, 6Tetrakisphosphate Octakis(Acetoxymethyl)Ester+sn-di-O-Palmitoyl-D,L-6-O-Butyryliphosphatidylinositol 3,4,5-Trisphosprate Heptakis(Acetoxymethyl)Ester The same experimental protocol of Example 8, above, was used with the following exception: PMNs isolated from human blood were preincubated with 200 μM vehicle, D-2,3-di-O-butyryl-myo-inositol 1,4,5,6-tetrakisphosphate octakis(acetoxymethyl)ester or 200 μM D-2,3-di-O-butyryl-myo-inositol 1,4,5,6 -tetrakisphosphate octakis (acetoxymethyl)ester+200 μM sn-di-O-palmitoyl-D,L-6-O-butyryl-phosphatidylinositol 3,4,5-trisphosphate heptakis (acetoxymethyl)ester for thirty minutes prior to addition of 1 μM f-MetLeuPhe stimulus and measurement of superoxide anion production. The resulting data, expressed as nmol superoxide anion/min/$10^7$ cells, and which represent separate aliquots of cells, are shown in Table 1, below:

TABLE 1

| | | Preincubation (30 min) | |
|---|---|---|---|
| Buffer control | Vehicle control | $Bt_2Ins(1,4,5,6)P_4$/AM | $Bt_2Ins(1,4,5,6)P_4$/AM + $diC_{16}$-6-O-Bt-PtdIns(3,4,5)P_3$/AM |
| 19.7 | 18.1 | 10.1 | 0.51 |
| 19.3 | 18.9 | 10.6 | 0.18 |
| | 21.1 | | |
| | 23.2 | | |

$Bt_2Ins(1, 4, 5, 6)P_4$/AM = D-2, 3-di-O-butyryl-myo-inositol 1, 4, 5, 6-tetrakisphosphate octakis(acetoxymethyl)ester.
$diC_{16}$-6-O-Bt-PtdIns(3, 4, 5)P_3$/AM = sn-di-O-palmitoyl-D, L-6-O-butyryl-phosphatidylinositol 3, 4, 5-trisphosphate heptakis(acetoxymethyl)ester.

As shown in Table 1, the superoxide anion-inhibiting ability of D-2,3-di-O-butyryl-myo-inositol 1,4,5, 6tetrakisphosphate octakis(acetoxymethyl)ester is additive with respect to that of sn-di-O-palmitoyl-D,L-6-O-butyryl-phosphatidylinositol 3,4,5-trisphosphate heptakis (acetoxymethyl)ester. Accordingly, it is believed that the mechanism for inhibition of superoxide anion by D-2,3-di-O-butyryl-myo-inositol 1,4,5,6-tetrakisphosphate octakis (acetoxymethyl)ester is different from the mechanism for inhibition by sn-di-O-palmitoyl-D,L-6-O-butyiyl-phosphatidylinositol 3,4,5-trisphosphate heptakis (acetoxymethyl)ester. Therefore, D-2,3-di-O-butyryl-myo-inositol 1,4,5,6-tetrakisphosphate octakis(acetoxymethyl) ester together with sn-di-O-palmitoyl-D,L-6-O-butyryl-phosphatidylinositol 3,4,5-trisphosphate heptakis (acetoxymethyl)ester, effectively inhibits superoxide anion production by human PMNs. Thus, D-2,3-di-O-butryl-myo-inositol 1,4,5,6-tetrakisphosphate octakis(acetoxymethyl) ester and sn-di-O-palmitoyl-D,L-6 -O-butyryl-phosphatidylinositol 3,4,5-trisphosphate keptakis (acetoxymethyl)ester are useful for inhibiting tissue damage caused by superoxide anion.

Inhibition of f-Methionine-Leucine-Phenylalanine-Stimulated Superoxide Anion Production in Human Neutrophils by D-2,3-di-O-Butyryl-Myo-Inositol 3,4,5-Trisphosphate Heptakis(Acetoxymethyl)Ester The same experimental protocol of Example 8, above, was used with the following exceptions: PMNs isolated from human blood were preincubated with 200 μM vehicle or sn-di-O-palmitoyl-D,L-6-O-butyryl-phosphatidylinositol 3,4,5-trisphosphate heptakis(acetoxymethyl)ester for thirty minutes prior to addition of f-MetLeuPhe or phorbol myristate acetate ("PMA," a non-physiological tumor promoter) stimulus and measurement of superoxide anion production. The resulting data, expressed as nmol superoxide anion/min/$10^7$ cells, are shown in Table 2, below:

TABLE 2

| Preincubation (10 min) | | | |
|---|---|---|---|
| Vehicle | | $diC_{16}$-6-O-Bt-PtdIns(3, 4, 5)$P_3$/AM | |
| f-MetLeuPhe | PMA | f-MetLeuPhe | PMA |
| 31.3 | 69 | 6.7 | 64.96 |
| 31 | 69.6 | 7.9 | 63.34 |

$diC_{16}$-6-O-Bt-PtdIns(3, 4, 5)$P_3$/AM = sn-di-O-palmitoyl-D, L-6-O-butyryl-phosphatidylinositol 3, 4, 5-trisphosphate heptakis(acetoxymethyl)ester.

As shown in Table 2, sn-di-O-palmitoyl-D,L-6-O-butyryl-phosphatidylinositol 3,4,5-trisphosphate heptakis (acetoxymethyl)ester only minimally inhibits superoxide anion production by PMNs stimulated with PMA. This finding indicates that the inhibitory ability of sn-di-O-palmitoyl-D,L-6-O-butyryl-phosphatidylinositol 3,4,5-trisphosphate heptakis(acetoxymethyl)ester is not due to any effect relating to toxicity or superoxide anion-scavenging ability, but rather to the signaling pathway involved when an in vivo signal, e.g., f-MetLeuPhe, leukotriene B4, complement factor Sa, triggers production of inositol derivatives.

11. EXAMPLE

Production of Phosphatidylinositol 3,4,5 Trisphosphate by f-Methionine-Leucine-Phenylalanine-Stimulated Neutrophils of a Crohn'S Disease Patient Neutrophils prepared from the blood of a patient with Crohn's Disease, a form of inflammatory bowel disease, were isolated and prepared by Hespan sedimentation and Percoll differential density centrifugation (G. Dobos et al., *J. Immunol.* 149(2):609–14 (1992)). The neutrophils so obtained had a degree of purity and viability of greater than 95%. Phosphatidylinositol 3,4,5-trisphosphate produced in response to stimulation with 1 μM f-MetLeuPhe was measured according to the procedure of A. E. Traynor-Kaplan et al., *J. Biol. Chem.* 264(26):15668–15673 (1989). The Crohn's Disease patient from which the neutrophils were taken had not been receiving steroids at the time the neutrophils were harvested. A control time point using neutrophils from non-Crohn's disease patients was selected based on peak phosphatidylinositol 3,4,5-trisphosphate production.

As shown in FIG. 4, f-MetLeuPhe-stimulated neutrophils of the Crohn's disease patient produced significantly lower levels of phosphatidylinositol 3,4,5-trisphosphate than did human neutrophils obtained from a non-Crohn's Disease patient (control). Phosphatidylinositol 3,4,5-trisphosphate is known to be produced by neutrophils in response to f-MetLeuPhe, and reduction of phosphatidylinositol 3,4,5-trisphosphate levels have been reported to correlate with reduced levels of superoxide anion (G. Dobos et al., *J. Immunol.* 149(2):609–14 (1992)). Accordingly, phosphatidylinositol 3,4,5-trisphosphate appears to inhibit superoxide anion production which Applicants believe occurs in neutrophils of healthy patients. That levels of phosphatidylinositol 3,4,5-trisphosphate produced by f-MetLeuPhe-stimulated neutrophils of a Crohm's Disease patient are lower than those of f-MetLeuPhe-stimulated neutrophils of a healthy patient suggests that adminstration of an inositol derivative to a patient experiencing inflammation, e.g., Crohn's disease, can inhibit superoxide anion production by providing a therapeutically effective amount of an inositol derviative to the site of inflammation.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited, the entire disclosures of which are incorporated herein by reference.

What is claimed is:

1. A method for inhibiting superoxide anion production, comprising administering to a mammal in need of such inhibition a therapeutically effective amount of a compound havin the formula (I):

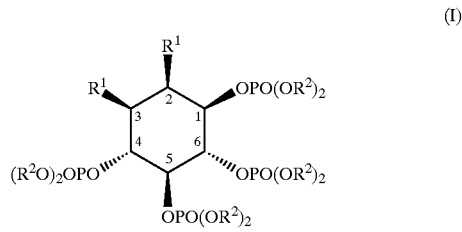

or a racemate thereof, or a pharmaceutically acceptable salt thereof, wherein each RW is independently selected from the group consisting of hydrogen, —OH, —$C_1$–$C_{20}$ straight or branched chain alkyl,—$C_2$–$C_{20}$ straight or branched chain alkenyl or alkynyl, —OC(O)$C_1$–$C_{20}$ straight or branched chain alkyl, —OC(O)$C_2$–$C_{20}$ straight or branched chain alkenyl or alkynyl, —O$C_1$–$C_{20}$ straight or branched chain alkyl, and —O$C_2$–$C_{20}$ straight or branched chain alkenyl or alkynyl;

each $R^2$ is independently selected from the group consisting of hydrogen and —C($R^3$)($R^3$)OC(O)$C_1$–$C_4$ straight or branched chain alkyl; and each $R^3$ is independently selected from the group consisting of hydrogen, —$C_1$–$C_{12}$ alkyl, phenyl, and benzyl, or both $R^3$ taken together form a 5- or 6-membered ring, said $R^3$, except hydrogen, being unsubstituted or substituted with one or more halogen, —OH, $C_1$–$C_6$ alkyl, $NO_2$, —O$C_1$–$C_6$ alkyl, and —OC (O)$C_1$–$C_6$ alkl groups.

2. The method of claim 1, wherein the superoxide anion production is caused by inflammation.

3. The method of claim 2, wherein the inflammation accompanies a condition selected from the group consisting of physical trauma, dermatitis, eczema, psoriasis, acute contact dermatitis, drug eruption, gastritis, inflammatory bowel disease, rheumatoid arthritis, non-rheumatoid arthritis, asthma, ischemia/reperfusion injury, ulcerative colitis, adult respiratory distress syndrome, smoke inhalation, heart attack, stroke, chronic lung disease, arthritis, alcoholic liver disease, xenobiotic toxicity and iron toxicity.

4. The methods of claim 1, wherein the compound is administered in a composition comprising a pharmaceutically acceptable carrier or vehicle.

5. The method of claim 4, wherein the composition further comprises a drug selected from the group consisting of a non-steroidal anti-inflammatory drug, a leukotriene antagonist and an anti-inflammatory agent.

6. The method of claim 5, wherein the non-steroidal anti-inflammatory drug is selected from the group consisting of salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, anpiroxicam, droxicam, pivoxicam, tenoxicam, nabumetome, phenylbutazone, oxyphenbutazone, antipyrine, aminopyrine, apazone and nimesulide.

7. The method of claim 5, wherein the leukotriene antagonist is selected from the group consisting of zileuton, aurothioglucose, gold sodium thiomalate and auranofin.

8. The method of claim 5, wherein the anti-inflammatory agent is selected from the group consisting of coichicine, allopurinol, probenecid, sulfinpyrazone and benzbromarone.

9. A method for inhibiting superoxide anion production, comprising contacting a cell or tissue with an effective amount of a compound having the general formula (I):

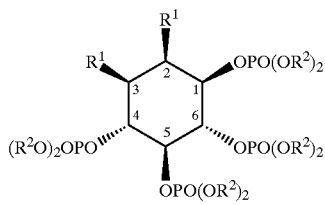

(I)

or a racemate thereof, or a pharmaceutically acceptable salt thereof, wherein each $R^1$ is independently selected from the group consisting of hydrogen, —OH, —$C_1$–$C_{20}$ straight or branched chain alkyl, —$C_2$–$C_{20}$ straight or branched chain alkenyl or alkynyl, —OC(O)$C_1$–$C_{20}$ straight or branched chain alkyl, —OC(O)$C_2$–$C_{20}$ straight or branched chain alkenyl or alkynyl, —O$C_1$–$C_{20}$ straight or branched chain alkyl, and —O$C_2$–$C_{20}$ straight or branched chain alkenyl or alkynyl;

each $R^2$ is independently selected from the group consisting of hydrogen and —C($R^3$)($R^3$)OC(O)$C_1$–$C_4$ straight or branched chain alkyl; and each $R^3$ is independently selected from the group consisting of hydrogen, —$C_1$–$C_{12}$ alkyl, phenyl, and benzyl, or both $R^3$ taken together form a 5- or 6-membered ring, said $R^3$, except hydrogen, being unsubstituted or substituted with one or more halogen, —OH, $C_1$–$C_6$ alkyl, $NO_2$, —O$C_1$–$C_6$ alkyl, and —OC(O)$C_1$–$C_6$ alkyl groups.

10. The method of claim 9, wherein the superoxide anion production is caused by inflammation.

11. The method of claim 10, wherein the inflammation accompanies a condition selected from the group consisting of physical trauma, dermatitis, eczema, psoriasis, acute contact dermatitis, drug eruption, gastritis, inflammatory bowel disease, rheumatoid arthritis, non-rheumatoid arthritis, asthma, ischemia/reperfusion injury, ulcerative colitis, adult respiratory distress syndrome, smoke inhalation, heart attack, stroke, chronic lung disease, arthritis, alcoholic liver disease, xenobiotic toxicity and iron toxicity.

12. The method of claim 11, wherein the compound is delivered in a composition comprising a pharmaceutically acceptable carrier or vehicle.

13. The method of claim 9, wherein the composition further comprises a drug selected from the group consisting of a non-steroidal anti-inflammatory drug, a leukotriene antagonist and an anti-inflammatory agent.

14. The method of claim 13, wherein the non-steroidal anti-inflammatory drug is selected from the group consisting of salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide.

15. The method of claim 13, wherein the leukotriene antagonist is selected from the group consisting of zileuton, aurothioglucose, gold sodium thiomalate and auranofin.

16. The method of claim 13, wherein the anti-inflammatory agent is selected from the group consisting of colchicine, allopurinol, probenecid, sulfinpyrazone and benzbromarone.

17. A method for inhibiting superoxide anion production, comprising administering to a mammal in need of such inhibition a therapeutically effective amount of a compound having the general formula (II):

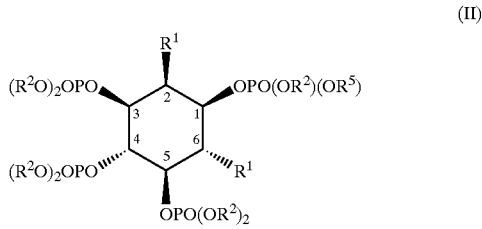

(II)

or an L-enantiomer or racemate thereof, or a pharmaceutically acceptable salt thereof, wherein each $R^1$ is independently selected from the group consisting of hydrogen, —OH, —$C_1$–$C_{20}$ straight or branched chain alkyl, —$C_2$–$C_{20}$ straight or branched chain alkenyl or alkynyl, —OC(O)$C_1$–$C_{20}$ straight or branched chain alkyl —OC(O)$C_2$–$C_{20}$ straight or branched chain alkenyl or alkynyl, —O$C_1$–$C_{20}$ straight or branched chain alkyl, and —O$C_2$–$C_{20}$ straight or branched chain alkenyl or alkynyl;

each $R^2$ is independently selected from the group consisting of hydrogen and —C($R^3$)($R^3$)OC(O)$C_1$–$C_4$ straight or branched chain alkyl;

each $R^3$ is independently selected from the group consisting of hydrogen, —$C_1$–$C_{12}$ alkyl, phenyl, benzyl, or both $R^3$ taken together form a 5- or 6-membered ring, said $R^3$, except hydrogen, being unsubstituted or substituted with one or more halogen, —OH, $C_1$–$C_6$ alkyl, $NO_2$, —O$C_1$–$C_6$ alkyl, and —OC(O)$C_1$–$C_6$ alkyl groups;

each $R^5$ is independently selected from the group consisting of hydrogen and —$CH_2CH(XR^6)CH_2XR^6$;

each $R^6$ is independently selected from the group consisting of hydrogen, —$C_1$–$C_{23}$ straight or branched chain alkyl —$C_2$–$C_{23}$ alkenyl and —$C_4$–$C_{23}$ alkadienyl; and each X is independently selected from the group consisting of —OC(O)—, —SC(O)—, —OC(S)—, —S— and —O—.

18. The method of claim 17, wherein the superoxide anion production is caused by inflammation.

19. The method of claim 18, wherein the inflammation accompanies a condition selected from the group consisting of physical trauma, dermatitis, eczema, psoriasis, acute contact dermatitis, drug eruption, gastritis, inflammatory bowel disease, rheumatoid arthritis, non-rheumatoid arthritis, asthma, ischemia/reperfusion injury, ulcerative colitis, adult respiratory distress syndrome, smoke inhalation, heart attack, stroke, chronic lung disease, arthritis, alcoholic liver disease, xenobiotic toxicity and iron toxicity.

20. The method of claim 17, wherein the compound is administered in a composition comprising a pharmaceutically acceptable carrier or vehicle.

21. The method of claim 20, wherein the composition further comprises a drug selected from the group consisting of a non-steroidal anti-inflammatory drug, a leukotriene antagonist and an anti-inflammatory agent.

22. The method of claim 21, wherein the non-steroidal anti-inflammatory drug is selected from the group consisting of salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide.

23. The method of claim 21, wherein the leukotriene antagonist is selected from the group consisting of zileuton, aurothioglucose, gold sodium thiomalate and auranofin.

24. The method of claim 21, wherein the anti-inflammatory agent is selected from the group consisting of colchicine, allopurinol, probenecid, sulfinpyrazone and benzbromarone.

25. A method for inhibiting superoxide anion production, comprising contacting a cell or tissue with an effective amount of a compound having the general formula (II):

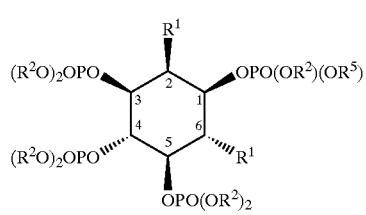

(II)

or an L-enantioner or racemate thereof, or a pharmaceutically acceptable salt thereof, wherein each $R^1$ is independently selected from the group consisting of hydrogen, —OH, —$C_1$–$C_2$. straight or branched chain alkyl, —$C_2$–$C_{20}$ straight or branched chain alkenyl or alkynyl, —OC(O)$C_1$–$C_{20}$ straight or branched chain alkyl, —OC(O)$C_2$–$C_{20}$ straigt or branched chain alkenyl or alkynyl, —O$C_1$–$C_{20}$ straight or branched chain alkyl, and —O$C_2$–$C_{20}$ straight or branched chain alkenyl or alkynyl;

each $R^2$ is independently selected from the group consisting of hydrogen and —C($R^3$)($R^3$)OC(O)$C_1$–$C_4$ straight or branched chain alkyl;

each $R^3$ is independently selected from the group consisting of hydrogen, —$C_1$–$C_{12}$ alkyl, phenyl, benzyl, or both le taken together form a 5- or 6-membered ring, said $R^3$, except hydrogen, being unsubstituted or substituted with one or more halogen, —OH, $C_1$–$C_6$ alkyl, $NO_2$, —O$C_1$–$C_6$ alkyL, and —OC(O)$C_1$–$C_6$ alkyl groups;

each $R^6$ is independently selected from the group consisting of hydrogen and —$CH_2CH(XR^6)CH_2XR^6$;

each $R^6$ is independently selected from the group consisting of hydrogen, —$C_1$–$C_{23}$ straight or branched chain alkyl, —$C_2$–$C_{23}$ alkenyl and —$C_4$–$C_{23}$ alkadienyl; and each X is independently selected from the group consisting of —OC(O)—, —SC(O)—, —OC(S)—, —S— and —O—.

26. The method of claim 25, wherein the superoxide anion production is caused by inflammation.

27. The method of claim 26, wherein the inflammation accompanies a condition selected from the group consisting of physical trauma, dermatitis, eczema, psoriasis, acute contact dermatitis, drug eruption, gastritis, inflammatory bowel disease, rheumatoid arthritis, non-rheumatoid arthritis, asthma, ischemia/reperfusion injury, ulcerative colitis, adult respiratory distress syndrome, smoke inhalation, heart attack, stroke, chronic lung disease, arthritis, alcoholic liver disease, xenobiotic toxicity and iron toxicity.

28. The method of claim 25, wherein the compound is delivered in a composition comprising a pharmaceutically acceptable carrier or vehicle.

29. The method of claim 28, wherein the composition further comprises a drug selected from the group consisting of a non-steroidal anti-inflammatory drug, a leukotriene antagonist and an anti-inflammatory agent.

30. The method of claim 28, wherein the non-steroidal anti-inflammatory drug is selected from the group consisting of salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide.

31. The method of claim 28, wherein the leukotriene antagonist is selected from the group consisting of zileuton, aurothioglucose, gold sodium thiomalate and auranofin.

32. The method of claim 28, wherein the anti-inflammatory agent is selected from the group consisting of colchicine, allopurinol, probenecid, sulfinpyrazone and benzbromarone.

33. The method of claim 1, wherein the compound of formula (I) is selected from the group consisting of:

D-myo-inositol 1,4,5,6-tetrakisphosphate;

D-2,3-di-O-methyl-myo-inositol 1,4,5,6-tetrakisphosphate octakis(acetoxymethyl) ester;

D-2-O-butyryl-3-O-methyl-myo-inositol 1,4,5,6-tetrakisphosphate octakis(acetoxymethyl) ester;

D-2-O-butyl-3-O-butyryl-myo-inositol 1,4,5,6-tetrakisphosphate octakis(acetoxymethyl) ester;

D-2,3-di-O-butyl-myo-inositol 1,4,5,6-tetrakisphosphate octakis(acetoxymethyl) ester;

D-3-O-butyl-2-O-butyryl-myo-inositol 1,4,5,6-tetrakisphosphate octakis(acetoxymethyl) ester;

D-2,3-di-O-butyryl-myo-inositol 1,4,5,6-tetrakisphosphate octakis(acetoxymethyl) ester;
a racemate thereof; and
a pharmaceutically acceptable salt thereof.
34. The method of claim 9, wherein the compound of formula (I) is selected from the group consisting of:
D-myo-inositol 1,4,5,6-tetrakisphosphate;
D-2,3-di-O-methyl-myo-inositol 1,4,5,6-tetrakisphosphate octakis(acetoxymethyl) ester;
D-2-O-butyryl-3-O-methyl-myo-inositol 1,4,5,6-tetrakisphosphate octakis(acetoxymethyl) ester;
D-2-O-butyl-3-O-butyryl-myo-inositol 1,4,5,6-tetrakisphosphate octakis(acetoxymethyl) ester;
D-2,3-di-O-butyl-myo-inositol 1,4,5,6-tetrakisphosphate octakis(acetoxymethyl) ester;
D-3-O-butyl-2-O-butyryl-myo-inositol 1,4,5,6-tetrakisphosphate octakis(acetoxymethyl) ester;
D-2,3-di-O-butyryl-myo-inositol 1,4,5,6-tetrakisphosphate octakis(acetoxymethyl) ester;
a racemate thereof; and
a pharmaceitucally acceptable salt thereof.
35. The method of claim 17, wherein the compound of formula (II) is selected from the group consisting of:
sn-di-O-palmnitoyl-D,L-6-O-butyryl-phosphatidylinositol 3,4,5-trisphosphate heptakis(acetoxymethyl)ester, or a D- or L-enantiomer thereof;
sn-di-O-octanoyl-D,L-6-O-butyryl-phosphatidylinositol 3,4,5-trisphosphate heptakis(acetoxymethyl)ester, or a D- or L-enantiomer thereof;
sn-di-O-palnitoyl-D,L-2-O-butyryl-phosphatidylinositol 3,4,5-trisphosphate heptakis(acetoxymethyl)ester, or a D- or L-enantiomer thereof;
sn-di-O-octanoyl-D,L-2-O-butyryl-phosphatidylinositol 3,4,5-trisphosphate heptakis(acetoxymethyl)ester, or a D- or L-enantiomer thereof;
sn-di-O-palmitoyl-D,L-2,6-di-O-butyryl-phosphatidylinositol 3,4,5-trisphosphate heptakis(acetoxymethyl)ester, or a D- or L-enantiomer thereof;
sn-di-O-octanoyl-D,L-2,6-di-O-butyryl-phosphatidylinositol 3,4,5-trisphosphate heptakis(acetoxymethyl)ester, or a D- or L-enantiomer thereof;
D-phosphatidylinositol 3,4,5-trisphosphate, or its corresponding L-enantiomer or racemate thereof;
sn-di-O-lauryl-D-phosphatidylinositol 3,4,5-trisphosphate heptakis(acetoxymethyl)ester, or its corresponding L-enantiomer or racemate thereof; and
sn-di-O-octanoyl-D-phosphatidylinositol 3,4,5-trisphosphate heptakis(acetoxymethyl)ester, or its corresponding L-enantiomer or racemate thereof;
sn-di-O-palmitoyl-D-phosphatidylinositol 3,4,5-trisphosphate heptakis(acetoxymethyl)ester, or its corresponding L-enantiomer or racemate thereof; and
pharmaceutically acceptable salts thereof.
36. The method of claim 25, wherein the compound of formula (II) is selected from the group consisting of
sn-di-O-palmitoyl-D,L-6-O-butyryl-phosphatidylinositol 3,4,5-trisphosphate heptakis(acetoxymethyl)ester, or a D- or L-enantiomer thereof;
sn-di-O-octanoyl-D,L-6-O-butyryl-phosphatidylinositol 3,4,5-trisphosphate heptakis(acetoxymethyl)ester, or a D- or L-enantiomer thereof;
sn-di-O-palmitoyl-D,L-2-O-butyryl-phosphatidylinositol 3,4,5-trisphosphate heptakis(acetoxymethyl)ester, or a D- or L-enantiomer thereof;
sn-di-O-octanoyl-D,L-2-O-butyryl-phosphatidylinositol 3,4,5-trisphosphate heptakis(acetoxymethyl)ester, or a D- or L-enantiomer thereof;

sn-di-O-palrnitoyl-D,L-2,6-di-O-butyryl-phosphatidylinositol 3,4,5-trisphosphate heptakis(acetoxymethyl)ester, or a D- or L-enantiomer thereof;
sn-di-O-octanoyl-D,L-2,6-di-O-butyryl-phosphatidylinositol 3,4,5-trisphosphate heptakis(acetoxymethyl)ester, or a D- or L-enantiomer thereof;
D-phosphatidylinositol 3,4,5-trisphosphate, or its corresponding L-enantiomer or racemate thereof;
sn-di-O-lauryl-D-phosphatidylinositol 3,4,5-trisphosphate heptakis(acetoxymethyl)ester, or its corresponding L-enantiomer or racemate thereof;
sn-di-O-octanoyl-D-phosphatidylinositol 3,4,5-trisphosphate heptakis(acetoxymethyl)ester, or its corresponding L-enantiomer or racemate thereof, sn-di-O-palrnitoyl-D-phosphatidylinositol 3,4,5-trisphosphate heptakis(acetoxymethyl)ester, or its corresponding L-enantiomer or racemate thereof; and
pharmaceutically acceptable salts thereof.
37. A compound having the formula (I):

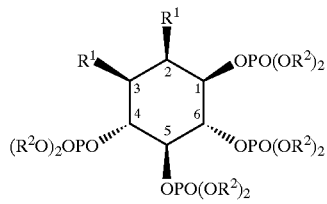

or a racemate thereof, or a pharmaceutically acceptable salt thereof,
wherein each $R^1$ is independently selected from the group consisting of hydrogen, —OH, —$C_1$–$C_{20}$ straight or branched chain alkyl, —$C_2$–$C_{20}$ straight or branched chain alkenyl or alkynyl, —OC(O)$C_1$–$C_{20}$ straight or branched chain alkyl, —OC(O)$C_2$–$C_{20}$ straight or branched chain alkenyl or alkynyl, —O$C_1$–$C_{20}$ straight or branched chain alkyl, and —O$C_2$–$C_{20}$ straight or branched chain alkenyl or alkynyl;
each $R^2$ is independently selected from the group consisting of hydrogen and —C($R^3$)($R^3$)OC(O)$C_1$–$C_4$ straight or branched chain alkyl; and
each $R^3$ is independently selected from the group consisting of hydrogen, —$C_1$–$C_{12}$ alkyl, phenyl, and benzyl, or both $R^3$ taken together form a 5- or 6-membered ring, said $R^3$, except hydrogen, being unsubstituted or substituted with one or more halogen, —OH, $C_1$–$C_6$ alkyl, $NO_2$, —O$C_1$–$C_6$ alkyl, and —OC(O)$C_1$–$C_6$ alkyl groups,
with the proviso that the compound of formula (I) is not:
D- or D,L-myoinositol 1,4,5,6-tetrakisphosphate;
D- or D,L-2,3-di-O-methyl-myo-inositol 1,4,5,6-tetrakisphosphate octakis(acetoxymethyl) ester;
D- or D,L-2-O-butyryl-3-O-methyl-myo-inositol 1,4,5,6-tetrakisphosphate octakis(acetoxymethyl) ester;
D- or D,L-2-O-butyl-3-O-butyryl-myo-inositol 1,4,5,6-tetrakisphosphate octakis(acetoxymethyl) ester;
D- or D,L-2,3-dideoxy-myo-inositol 1,4,5,6-tetrakisphosphate octakis(acetoxymethyl)ester;
D- or D,L-2,3-di-O-butyl-myo-inositol 1,4,5,6-tetrakisphosphate octakis(acetoxymethyl) ester;
D- or D,L-3-O-butyl-2-O-butyryl-myo-inositol 1,4,5,6-tetrakisphosphate octakis(acetoxymethyl) ester;
D- or D,L-2,3-di-O-butyryl-myo-inositol 1,4,5,6-tetrakisphosphate octakis(acetoxymethyl) ester;

D- or D,L-3-O-butyryl-2-deoxy-myo-inositol 1,4,5,6-tetrakisphosphate octakis(acetoxymethyl) ester;

D,L-2-O-butyryl-1-deoxy-myo-inositol 3,4,5,6-tetrakisphosphate octakis(acetoxymethyl) ester;

D,L-1-O-butyryl-2-O-methyl-myo-inositol 3,4,5,6-tetrakisphosphate octakis(acetoxymethyl) ester; or D,L-1,2-cyclohexylidene-myo-inositol 1,4,5,6-tetrakisphosphate octakis(acetoxymethyl)ester.

38. A compound having the formula (II):

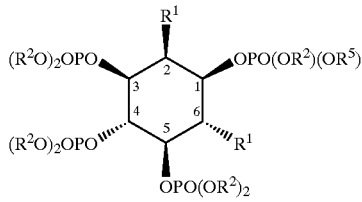

(II)

or an L-enantiomer or racemate thereof, or a pharmaceutically acceptable salt thereof, wherein each $R^1$ is independently selected from the group consisting of hydrogen, —OH, —$C_1$–$C_{20}$ straight or branched chain alkyl, —$C_2$–$C_{20}$ straight or branched chain alkenyl or alkynyl, —OC(O)$C_1$–$C_{20}$ straight or branched chain alkyl, —OC(O)$C_2$–$C_{20}$ straight or branched chain alkenyl or alkynyl, —O$C_1$–$C_{20}$ straight or branched chain alky, and —O$C_2$–$C_{20}$ straight or branched chain alkenyl or alkynyl;

each $R^2$ is independently selected from the group consisting of hydrogen and —C($R^3$)($R^3$)OC(O)$C_1$–$C_4$ straight or branched chain alkyl;

each $R^3$ is independently selected from the group consisting of hydrogen, —$C_1$–$C_{12}$ alkyl phenyl, and benzyl, or both $R^3$ taken together form a 5- or 6-membered ring, said $R^3$, except hydrogen, being unsubstituted or substituted with one or more halogen, —OH, $C_1$–$C_6$ alkyl, $NO_2$, —O$C_1$–$C_6$ alkyl, and —OC(O)$C_1$–$C_6$ alkyl groups;

each $R^5$ is independently selected from the group consisting of hydrogen and $CH_2CH(XR^6)CH_2XR^6$;

each $R^6$ is independently selected from the group consisting of hydrogen, —$C_1$–$C_{23}$ straight or branched chain alkyl, —$C_2$–$C_{23}$ alkenyl and —$C_4$–$C_{23}$ alkadienyl; and each X is independently selected from the group consisting of —OC(O)—, —C(O)—, —OC(S)—, —S— and —O—, with the proviso that the compound of formula (II) is not:

sn-di-O-palmitoyl-D,L-6-O-butyryl-phosphatidylinositol 3,4,5-trisphosphate eptakis(acetoxymethyl)ester;

sn-di-O-octanoyl-D,L-6-O-butyryl-phosphatidylinositol 3,4,5-trisphosphate eptakis(acetoxymethyl)ester;

sn-di-O-palhnitoyl-D,L-2-O-butyryl-phosphatidylinositol 3,4,5-trisphosphate eptakis(acetoxymethyl)ester;

sn-di-O-octanoyl-D,L-2-O-butyryl-phosphatidylinositol 3,4,5-trisphosphate eptakis(acetoxymethyl)ester;

sn-di-O-palmitoyl-D,L-2,6-di-O-butyryl-phosphatidylinositol 3,4,5-trisphosphate heptakis(acetoxymethyl)ester;

sn-di-O-octanoyl-D,L-2,6-di-O-butyryl-phosphatidylinositol 3,4,5-trisphosphate heptakis(acetoxymethyl)ester;

D- or D,L-phosphatidylinositol 3,4,5-trisphosphate;

sn-di-O-lauryl-D- or sn-di-O-lauryl-D,L-phosphatidylinositol 3,4,5-trisphosphate heptakis(acetoxymethyl)ester;

sn-di-O-octanoyl-D- or sn-di-O-octanoyl-D,L-phosphatidylinositol 3,4,5-trisphosphate heptakis(acetoxymethyl)ester; or sn-di-O-palmitoyl-D- or sn-di-O-palmitoyl-D,L-phosphatidylinositol 3,4,5-trisphosphate heptakis(acetoxymethyl)ester.

39. A pharmaceutical composition, comprising a therapeutically effective amount of a compound of claim 37 or a pharmaceutically acceptable salt thereof, and a physiologically acceptable carrier or vehicle.

40. The composition of claim 39, further comprising a therapeutic agent selected from the group consisting of a non-steroidal anti-inflammatory drug, a leukotriene antagonist and an anti-inflammatory agent.

41. The composition of claim 40, wherein the non-steroidal anti-inflammatory drug is selected from the group consisting of salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicamn, droxicam, pivoxicam, tenoxicam, nabumetome, phenylbutazone, oxyphenbutazone, antipyrine, aminopyrine, apazone and nimesulide.

42. The composition of claim 40, wherein the leukotriene antagonist is selected from the group consisting of zileuton, aurothioglucose, gold sodium thiomalate and auranofin.

43. The composition of claim 40, wherein the anti-inflammatory agent is selected from the group consisting of colchicine, allopurinol, probenecid, sulfinpyrazone and benzbromarone.

44. The composition of claim 39, wherein the composition is in the form of a tablet, pellet, capsule, capsule containing liquid, suppository, solution, emulsion, aerosol, spray or suspension.

45. A pharmaceutical composition, comprising a therapeutically effective amount of a compound of claim 38 or a pharmaceutically acceptable salt thereof, and a physiologically acceptable carrier or vehicle.

46. The composition of claim 45, further comprising a therapeutic agent selected from the group consisting of a non-steroidal anti-inflammatory drug, a leukotriene antagonist and an anti-inflammatory agent.

47. The composition of claim 46, wherein the non-steroidal anti-inflammatory drug is selected from the group consisting of salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide.

48. The composition of claim 46, wherein the leukotriene antagonist is selected from the group consisting of zileuton, aurothioglucose, gold sodium thiomalate and auranofin.

49. The composition of claim 46, wherein the anti-inflammatory agent is selected from the group consisting of colchicine, allopurinol, probenecid, sulfinpyrazone and benzbromarone.

50. The composition of claim 45, wherein the composition is in the form of a tablet, pellet, capsule, capsule containing liquid, suppository, solution, emulsion, aerosol, spray or suspension.

* * * * *

UNITED STATES PATENT AND TRADEMARK OFFICE
CERTIFICATE OF CORRECTION

PATENT NO. : 6,221,856 B1
DATED : April 24, 2001
INVENTOR(S) : A.E. Traynor-Kaplan et al.

It is certified that error appears in the above-identified patent and that said Letters Patent is hereby corrected as shown below:

Title page,
References Cited,
"Tetrak-isphosphate" should be hyphenated -- Tetra-kisphosphate --
"Alzhe-imer's" should be hyphenated -- Alz-heimer's --
"1998," should read -- 1988 --

Column 26,
Line 18, "havin" should read -- having --
Line 32, "RW" should read -- $R^1$ --
Line 50, "alkl" should read -- alkyl --

Column 28,
Line 24-25, "ben-zbromarone." should be hyphenated -- benz-bromarone. --
Line 48, "alkyl" should read -- alkyl, --
Line 62, "$R^5$is" should read -- $R^5$ is --
Line 66, "alkyl" should read -- alkyl, --

Column 29,
Line 39-40, "ben-zbromarone." should be hyphenated -- benz-bromarone. --
Line 58, "-$C_2$." should read -- -$C_{20}$ --
Line 61, "straigt" should read -- straight --

Column 30,
Line 3, "Ie" should read -- $R^3$ --
Line 6, "alkyL," should read -- alkyl, --
Line 8, "$R^6$" should read -- $R^5$ --
Line 52-53, "ben-zbromarone." should be hyphenated -- benz-bromarone. --

Column 31,
Line 24, "palmnitoyl" should read -- palmitoyl --
Line 31, "palnitoyl" should read -- palmitoyl --

Column 32,
Line 1, "palrnitoyl" should read -- palmitoyl --
Line 14, "thereof," should read -- thereof; -- and a new subparagraph should begin thereafter
Line 15, "palrnitoyl" should read -- palmitoyl --
Line 53, "myoinositol" should read -- myo-inositol --

UNITED STATES PATENT AND TRADEMARK OFFICE
CERTIFICATE OF CORRECTION

PATENT NO.    : 6,221,856 B1
DATED         : April 24, 2001
INVENTOR(S)   : A.E. Traynor-Kaplan et al.

It is certified that error appears in the above-identified patent and that said Letters Patent is hereby corrected as shown below:

Column 33,
Line 34, "alkyl" should read -- alkyl, --
Line 42, "CH$_2$" should read -- -CH$_2$ --
Line 47, "-C(O)-," should read -- SC(O)-, --
Line 51, "eptakis" should read -- heptakis --
Line 53, "eptakis" should read -- heptakis --
Line 54, "palhnitoyl" should read -- palmitoyl --
Line 55, "eptakis" should read -- heptakis --
Line 57, "eptakis" should read -- heptakis --

Column 34,
Line 23, "ampiroxicamn" should read -- ampiroxicam --
Line 60-61, "ben-zbromarone." should be hyphenated -- benz-bromarone. --

Signed and Sealed this

Twenty-sixth Day of February, 2002

Attest:

*Attesting Officer*

JAMES E. ROGAN
*Director of the United States Patent and Trademark Office*